(12) United States Patent
Coulthard

(10) Patent No.: US 8,267,908 B2
(45) Date of Patent: Sep. 18, 2012

(54) DELIVERY TUBE, SYSTEM, AND METHOD FOR STORING LIQUID FROM A TISSUE SITE

(75) Inventor: Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 578 days.

(21) Appl. No.: 12/275,417

(22) Filed: Nov. 21, 2008

(65) Prior Publication Data
US 2009/0124988 A1    May 14, 2009

Related U.S. Application Data

(63) Continuation-in-part of application No. 12/069,363, filed on Feb. 8, 2008.

(60) Provisional application No. 60/900,415, filed on Feb. 9, 2007.

(51) Int. Cl.
*A61M 1/00* (2006.01)

(52) U.S. Cl. ............. 604/313; 604/66; 604/67; 604/35; 604/118; 604/119; 604/289; 604/290; 604/304; 604/305; 604/308; 604/315; 604/317; 604/318; 604/319; 604/322; 604/327; 604/541; 604/543; 600/573; 600/578; 600/29; 600/30; 600/31; 600/32

(58) Field of Classification Search .................. 604/313, 604/315, 317, 318, 319
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,376,868 A | 4/1968 | Mondiadis |
| 3,382,867 A | 5/1968 | Reaves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |

(Continued)

FOREIGN PATENT DOCUMENTS
AU    550575 A1    8/1982
(Continued)

OTHER PUBLICATIONS

Final Office Action date mailed Dec. 7, 2010 for U.S. Appl. No. 12/069,363.

(Continued)

*Primary Examiner* — Tatyana Zalukaeva
*Assistant Examiner* — Ilya Treyger

(57) ABSTRACT

An apparatus, system, and method for storing liquid from a tissue site are presented. The apparatus includes a delivery tube that may have at least one lumen. The delivery tube may be operable to transmit reduced pressure to the tissue site and to receive liquid from the tissue site. The apparatus may also include an absorbent material disposed in the at least one lumen. The absorbent material may be operable to absorb the liquid from the tissue site. The delivery tube may be formed with a number of recesses.

19 Claims, 12 Drawing Sheets

U.S. PATENT DOCUMENTS

| | | |
|---|---|---|
| 3,774,611 A | 11/1973 | Tussey et al. |
| 3,779,243 A | 12/1973 | Tussey et al. |
| 3,823,716 A | 7/1974 | Hale |
| 3,826,254 A | 7/1974 | Mellor |
| 3,875,941 A | 4/1975 | Adair |
| 3,957,054 A * | 5/1976 | McFarlane .................. 604/541 |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,250,882 A | 2/1981 | Adair |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,329,743 A | 5/1982 | Alexander et al. |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,433,973 A | 2/1984 | Kurtz et al. |
| 4,465,485 A | 8/1984 | Kashmer et al. |
| 4,475,909 A | 10/1984 | Eisenberg |
| 4,480,638 A | 11/1984 | Schmid |
| 4,523,920 A | 6/1985 | Russo |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,573,965 A | 3/1986 | Russo |
| 4,579,555 A | 4/1986 | Russo |
| 4,605,399 A | 8/1986 | Weston et al. |
| 4,608,041 A | 8/1986 | Nielson |
| 4,640,688 A | 2/1987 | Hauser |
| 4,642,093 A | 2/1987 | Harle |
| 4,643,719 A | 2/1987 | Garth et al. |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,981,474 A | 1/1991 | Bopp et al. |
| 4,985,019 A | 1/1991 | Michelson |
| 5,013,300 A | 5/1991 | Williams |
| 5,019,059 A | 5/1991 | Goldberg et al. |
| 5,034,006 A | 7/1991 | Hosoda et al. |
| 5,037,397 A | 8/1991 | Kalt et al. |
| 5,086,170 A | 2/1992 | Luheshi et al. |
| 5,092,858 A | 3/1992 | Benson et al. |
| 5,100,395 A | 3/1992 | Rosenberg |
| 5,100,396 A | 3/1992 | Zamierowski |
| 5,102,404 A | 4/1992 | Goldberg et al. |
| 5,108,364 A | 4/1992 | Takezawa et al. |
| 5,112,323 A | 5/1992 | Winkler et al. |
| 5,116,310 A | 5/1992 | Seder et al. |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,259,399 A | 11/1993 | Brown |
| 5,261,893 A | 11/1993 | Zamierowski |
| 5,266,071 A | 11/1993 | Elftman |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,358,494 A | 10/1994 | Svedman |
| 5,405,322 A | 4/1995 | Lennox et al. |
| 5,437,622 A | 8/1995 | Carion |
| 5,437,651 A | 8/1995 | Todd et al. |
| 5,470,316 A | 11/1995 | Tovey et al. |
| 5,527,293 A | 6/1996 | Zamierowski |
| 5,549,579 A | 8/1996 | Batdorf et al. |
| 5,549,584 A | 8/1996 | Gross |
| 5,556,375 A | 9/1996 | Ewall |
| 5,569,184 A | 10/1996 | Crocker et al. |
| 5,607,388 A | 3/1997 | Ewall |
| 5,636,643 A | 6/1997 | Argenta et al. |
| 5,643,589 A | 7/1997 | Chalmers |
| 5,645,081 A | 7/1997 | Argenta et al. |
| 5,676,634 A | 10/1997 | Khouri |
| 5,713,874 A | 2/1998 | Ferber |
| 5,735,833 A | 4/1998 | Olson |
| 5,738,656 A | 4/1998 | Wagner |
| 5,762,640 A | 6/1998 | Kajiwara et al. |
| 5,820,581 A | 10/1998 | Wolfinbarger, Jr. |
| 5,914,264 A | 6/1999 | Korman |
| 5,941,859 A | 8/1999 | Lerman |
| 5,980,503 A | 11/1999 | Chin |
| 5,984,942 A | 11/1999 | Alden et al. |
| 6,042,537 A | 3/2000 | Kaiser |
| 6,071,267 A | 6/2000 | Zamierowski |
| 6,080,243 A | 6/2000 | Insley et al. |
| 6,135,116 A | 10/2000 | Vogel et al. |
| 6,142,982 A | 11/2000 | Hunt et al. |
| 6,174,306 B1 | 1/2001 | Fleischmann |
| 6,241,747 B1 | 6/2001 | Ruff |
| 6,287,316 B1 | 9/2001 | Agarwal et al. |
| 6,345,623 B1 | 2/2002 | Heaton et al. |
| 6,394,948 B1 | 5/2002 | Borst et al. |
| 6,398,767 B1 | 6/2002 | Fleischmann |
| 6,458,109 B1 | 10/2002 | Henley et al. |
| 6,478,789 B1 | 11/2002 | Spehalski et al. |
| 6,488,643 B1 | 12/2002 | Tumey et al. |
| 6,493,568 B1 | 12/2002 | Bell et al. |
| 6,500,112 B1 | 12/2002 | Khouri |
| 6,551,280 B1 | 4/2003 | Knighton et al. |
| 6,553,998 B2 | 4/2003 | Heaton et al. |
| 6,572,594 B2 | 6/2003 | Satterfield et al. |
| 6,626,891 B2 | 9/2003 | Ohmstede |
| 6,641,553 B1 | 11/2003 | Chee |
| 6,641,575 B1 | 11/2003 | Lonky |
| 6,648,862 B2 * | 11/2003 | Watson .................. 604/319 |
| 6,656,149 B2 | 12/2003 | Ladd |
| 6,660,484 B2 | 12/2003 | Charych et al. |
| 6,682,506 B1 | 1/2004 | Navarro |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,755,796 B2 | 6/2004 | Spector |
| 6,755,807 B2 | 6/2004 | Risk, Jr. et al. |
| 6,758,836 B2 | 7/2004 | Zawacki |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,840,960 B2 | 1/2005 | Bubb |

| | | |
|---|---|---|
| 6,855,135 B2 | 2/2005 | Lockwood et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,077,832 B2 | 7/2006 | Fleischmann |
| 7,128,735 B2 | 10/2006 | Weston |
| 7,195,624 B2 | 3/2007 | Lockwood et al. |
| 7,276,051 B1 | 10/2007 | Henley et al. |
| 7,344,512 B2 | 3/2008 | Yamazaki et al. |
| 7,396,339 B2 | 7/2008 | Britto et al. |
| 7,699,823 B2 * | 4/2010 | Haggstrom et al. ........... 604/313 |
| 7,824,384 B2 | 11/2010 | Watson, Jr. |
| 7,976,533 B2 | 7/2011 | Larsson |
| 8,057,449 B2 | 11/2011 | Sanders et al. |
| 2002/0065494 A1 | 5/2002 | Lockwood et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0161346 A1 | 10/2002 | Lockwood et al. |
| 2002/0198503 A1 | 12/2002 | Risk, Jr. et al. |
| 2002/0198504 A1 | 12/2002 | Risk, Jr. et al. |
| 2003/0014022 A1 | 1/2003 | Lockwood et al. |
| 2003/0057070 A1 | 3/2003 | Wang et al. |
| 2003/0088209 A1 | 5/2003 | Chiu et al. |
| 2003/0187367 A1 | 10/2003 | Odland |
| 2003/0216672 A1 | 11/2003 | Rastegar et al. |
| 2003/0225441 A1 | 12/2003 | Boynton et al. |
| 2004/0006319 A1 | 1/2004 | Lina et al. |
| 2004/0039406 A1 | 2/2004 | Jessen |
| 2004/0064111 A1 | 4/2004 | Lockwood et al. |
| 2004/0064132 A1 | 4/2004 | Boehringer et al. |
| 2004/0093026 A1 | 5/2004 | Weidenhagen et al. |
| 2005/0004534 A1 | 1/2005 | Lockwood et al. |
| 2005/0065484 A1 | 3/2005 | Watson, Jr. |
| 2005/0070858 A1 | 3/2005 | Lockwood et al. |
| 2005/0131327 A1 | 6/2005 | Lockwood et al. |
| 2005/0137539 A1 | 6/2005 | Biggie et al. |
| 2005/0148913 A1 | 7/2005 | Weston |
| 2005/0171467 A1 | 8/2005 | Landman |
| 2005/0203483 A1 | 9/2005 | Perkins et al. |
| 2005/0245906 A1 | 11/2005 | Makower et al. |
| 2005/0261642 A1 | 11/2005 | Weston |
| 2005/0261643 A1 | 11/2005 | Bybordi et al. |
| 2006/0149170 A1 | 7/2006 | Boynton et al. |
| 2006/0271019 A1 | 11/2006 | Stoller et al. |
| 2007/0021698 A1 | 1/2007 | Fleischmann |
| 2007/0078366 A1 | 4/2007 | Haggstrom et al. |
| 2007/0118096 A1 | 5/2007 | Smith et al. |
| 2008/0275409 A1 | 11/2008 | Kane et al. |
| 2009/0216170 A1 | 8/2009 | Robinson et al. |
| 2009/0227969 A1 | 9/2009 | Jaeb et al. |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | S58-95841 U | 6/1983 |
| JP | 4129536 | 4/1992 |
| JP | 6-70746 U | 10/1994 |
| JP | H11-501837 | 2/1999 |
| JP | 2001-252349 | 9/2001 |
| JP | 2005-528167 | 9/2005 |
| SG | 71559 | 4/2002 |
| TW | 558444 | 10/2003 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 03/057070 | 7/2003 |
| WO | WO 2005/105180 A1 | 11/2005 |
| WO | WO 2007/019038 A2 | 2/2007 |
| WO | WO 2007/133618 A2 | 11/2007 |
| WO | WO 2009/126102 A1 | 10/2009 |

OTHER PUBLICATIONS

Response filed Jan. 28, 2011 for U.S. Appl. No. 12/069,363.
Non-Final Office Action date mailed Feb. 11, 2011 for U.S. Appl. No. 12/069,363.
Non-Final Office Action date mailed Feb. 14, 2011 for U.S. Appl. No. 11/724,072.
Advisory Action date mailed Nov. 10, 2010 for U.S. Appl. No. 11/807,834.
RCE/Response filed Nov. 24, 2010 for U.S. Appl. No. 11/807,834.
Non-Final Office Action date mailed Feb. 18, 2011 for U.S. Appl. No. 11/807,834.
N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (copy and certified translation).
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, Managing Draining Wounds and Fistulae: "New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164 (copy and certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

NPD 1000 Negative Pressure Wound Therapy System, Kalypto Medical, pp. 1-4.

Marc G. Jeschke, MD, et al: "Development of New Reconstructive Techniques: Use of Integra in Combination with Fibrin Glue and Negative-Pressure Therapy for Reconstruction of Acute and Chronic Wounds"; Plastic and Reconstructive Surgery, Feb. 2004, vol. 113, No. 2, pp. 525-530.

C. Daniel Medical, Inc.; All Silicone Jackson Pratt(r) Style Round Drain; www.cdanielmedical.com Mar. 2007, 2 pgs.

C. Daniel Medical, Inc.; All Silicone Jackson Pratt(r) Style Flat Drain; www.cdanielmedical.com; Mar. 2007, 2 pgs.

V.A.C.® Therapy Clinical Guidelines: A Reference Source for Clinicians (Jul. 2007).

Restriction Requirement date mailed Apr. 13, 2010 in U.S. Appl. No. 12/069,363.

Response to Restriction Requirement mailed May 4, 2010 in U.S. Appl. No. 12/069,363.

Non-Final Office Action dated Sep. 27, 2006 in U.S. Appl. No. 11/200,837.

Response filed Jan. 29, 2007 to Non-Final Office Action dated Sep. 27, 2006 in U.S. Appl. No. 11/200,837.

Final Office Action dated Apr. 27, 2007 in U.S. Appl. No. 11/200,837.

Response filed Jun. 26, 2007 to Final Office Action dated Apr. 27, 2007 in U.S. Appl. No. 11/200 837.

Advisory Action dated Jul. 26, 2007 in U.S. Appl. No. 11/200,837.

Request for Continued Examination filed Oct. 29, 2007 in U.S. Appl. No. 11/200,837.

Non-Final Office Action dated Jan. 16, 2008 in U.S. Appl. No. 11/200,837.

Response filed Mar. 27, 2008 to Non-Final Office Action dated Jan. 16, 2008 in U.S. Appl. No. 11/200,837.

Final Office Action dated Jul. 9, 2008 in U.S. Appl. No. 11/200,837.

Response filed Sep. 8, 2008 to Final Office Action dated Jul. 9, 2008 in U.S. Appl. No. 11/200,837.

Final Office Action dated Nov. 14, 2008 in U.S. Appl. No. 11/200,837.

Supplemental Response filed Feb. 27, 2009 to Final Office Action date mailed Nov. 14, 2008 in U.S. Appl. No. 11/200,837.

Restriction Requirement date mailed Mar. 5, 2009 in U.S. Appl. No. 11/200,837.

Response filed Apr. 3, 2009 to Restriction Requirement dated Mar. 5, 2009 in U.S. Appl. No. 11/200,837.

Non-Final Office Action date mailed Jul. 9, 2009 in U.S. Appl. No. 11/200,837.

Response filed Sep. 17, 2009 to Non-Final Action dated Jul. 9, 2009 in U.S. Appl. No. 11/200,837.

Notice of Allowance and Notice of Allowability date mailed Jan. 14, 2010 in U.S. Appl. No. 11/200,837.

RCE/Amendment filed Apr. 7, 2010 in U.S. Appl. No. 11/200,837.

Non-Final Office Action date mailed Jun. 18, 2009 in U.S. Appl. No. 11/807,834.

Response filed Aug. 19, 2009 to Non-Final Action dated Jun. 18, 2009 in U.S. Appl. No. 11/807,834.

Final Rejection date mailed Oct. 2, 2009 in U.S. Appl. No. 11/807,834.

RCE/Amendment filed Jan. 27, 2010 in U.S. Appl. No. 11/807,834.

Non-Final Rejection date mailed Mar. 11, 2010 in U.S. Appl. No. 11/807,834.

Express Abandonment filed Apr. 22, 2010 in U.S. Appl. No. 12/540,934.

Decision on Petition for Express Abandonment date and Notice of Abandonment date mailed May 3, 2010 in U.S. Appl. No. 12/540,934.

International Search Report and Written Opinion date mailed Jun. 28, 2010 for PCT Application No. PCT/US2009/064972.

Non-Final Office Action date mailed Jul. 9, 2010 for U.S. Appl. No. 12/069,363.

Notice of Allowance date mailed Jun. 16, 2010 for U.S. Appl. No. 11/200,837.

Interview Summary date mailed Jun. 11, 2010 for U.S. Appl. No. 11/807,834.

Response filed Jun. 14, 2010 for U.S. Appl. No. 11/807,834.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
Response filed Sep. 24, 2010 for U.S. Appl. No. 12/069,363.
Interview Summary date mailed Oct. 4, 2010 for U.S. Appl. No. 12/069,363.
Final Office Action date mailed Aug. 31, 2010 for U.S. Appl. No. 11/807,834.
Response filed Oct. 26, 2010 for U.S. Appl. No. 11/807,834.
Restriction Requirement date mailed Oct. 7, 2010 for U.S. Appl. No. 11/724,072.
Response filed Nov. 8, 2010 for U.S. Appl. No. 11/724,072.
Interview Summary date mailed May 2, 2011 for U.S. Appl. No. 11/724,072.
Response filed May 12, 2011 for U.S. Appl. No. 11/724,072.
Response filed May 16, 2011 for U.S. Appl. No. 11/807,834.
Interview Summary date mailed May 17, 2011 for U.S. Appl. No. 11/807,834.
Response filed Apr. 21, 2011 for U.S. Appl. No. 12/069,363.
International Search Report and Written Opinion date mailed May 6, 2010; PCT International Application No. PCT/US2009/061439.
Restriction Requirement date mailed Jul. 25, 2011 for U.S. Appl. No. 11/717,893.
Response filed Aug. 12, 2011 for U.S. Appl. No. 11/717,893.
Notice of Allowance date mailed Jul. 1, 2011 for U.S. Appl. No. 12/069,363.
Final Office Action date mailed Aug. 1, 2011 for U.S. App. No. 11/724,072.
Non-Final Office Action date mailed Jun. 30, 2011 for U.S. Appl. No. 11/807,834.
Non-Final Office Action date mailed Oct. 4, 2011 for U.S. Appl. No. 11/717,893.
Express Abandonment filed Nov. 29, 2011 for U.S. Appl. No. 11/724,072.

* cited by examiner

DELIVERY TUBE, SYSTEM, AND METHOD FOR STORING LIQUID FROM A TISSUE SITE

CROSS-REFERENCE TO RELATED APPLICATIONS

This application is a continuation-in-part of, and claims the benefit of, U.S. patent application Ser. No. 12/069,363, filed on Feb. 8, 2008, which claims the benefit of and priority to U.S. Provisional Application No. 60/900,415, filed Feb. 9, 2007. Each application is incorporated by reference for all purposes.

BACKGROUND OF THE INVENTION

1. Field of the Invention

The present invention relates generally to the field of tissue treatment, and more specifically to a system and method for storing liquid from a tissue site.

2. Description of Related Art

Clinical studies and practice have shown that providing a reduced pressure in proximity to a tissue site augments and accelerates the growth of new tissue at the tissue site. The applications of this phenomenon are numerous, but the application of reduced pressure has been particularly successful in treating wounds. The treatment of wounds using reduced pressure is sometimes referred to in the medical community as "negative pressure tissue treatment," "reduced pressure therapy," or "vacuum therapy." This type of treatment provides a number of benefits, including faster healing, and increased formulation of granulation tissue.

Reduced pressure treatment systems are often applied to large, highly exudating wounds present on patients undergoing acute or chronic care, as well as other severe wounds that are not readily susceptible to healing without application of reduced pressure. Low-severity wounds that are smaller in volume and produce less exudate have generally been treated using advanced dressings instead of reduced pressure treatment.

BRIEF SUMMARY

To alleviate the existing problems with reduced pressure treatment systems, the illustrative embodiments described herein are directed to an apparatus, system, and method for storing liquid from a tissue site. According to one illustrative embodiment, an apparatus includes a delivery tube, which may have at least one lumen, and that is operable to transmit reduced pressure to the tissue site and to receive liquid from the tissue site. The apparatus may also include an absorbent material disposed in the at least one lumen. The absorbent material may be operable to absorb the liquid from the tissue site. In another embodiment, no absorbent material is contained in the at least one lumen.

According to another illustrative embodiment, a system for storing liquid from a tissue site is also provided that may include a reduced pressure source operable to supply reduced pressure, a manifold adapted to distribute the reduced pressure, a delivery tube having at least one lumen, and an absorbent material disposed in the at least one lumen.

According to another illustrative embodiment, a method for storing liquid from a tissue site includes placing a delivery tube having at least one lumen in fluid communication with a tissue site, supplying a reduced pressure to the at least one lumen such that liquid from the tissue site is drawn into the at least one lumen, and absorbing the liquid from the tissue site using an absorbent material in the at least one lumen such that the liquid from the tissue site is stored in the at least one lumen.

According to another illustrative embodiment, a method of manufacturing an apparatus for storing liquid from a tissue site is also provided. The method may include forming a delivery tube having at least one lumen and providing an absorbent material. The method may also include applying an absorbent material in the at least one lumen.

Other objects, features, and advantages of the illustrative embodiments will become apparent with reference to the drawings and detailed description that follow.

DETAILED DESCRIPTION OF THE PREFERRED EMBODIMENT

Figure 1:
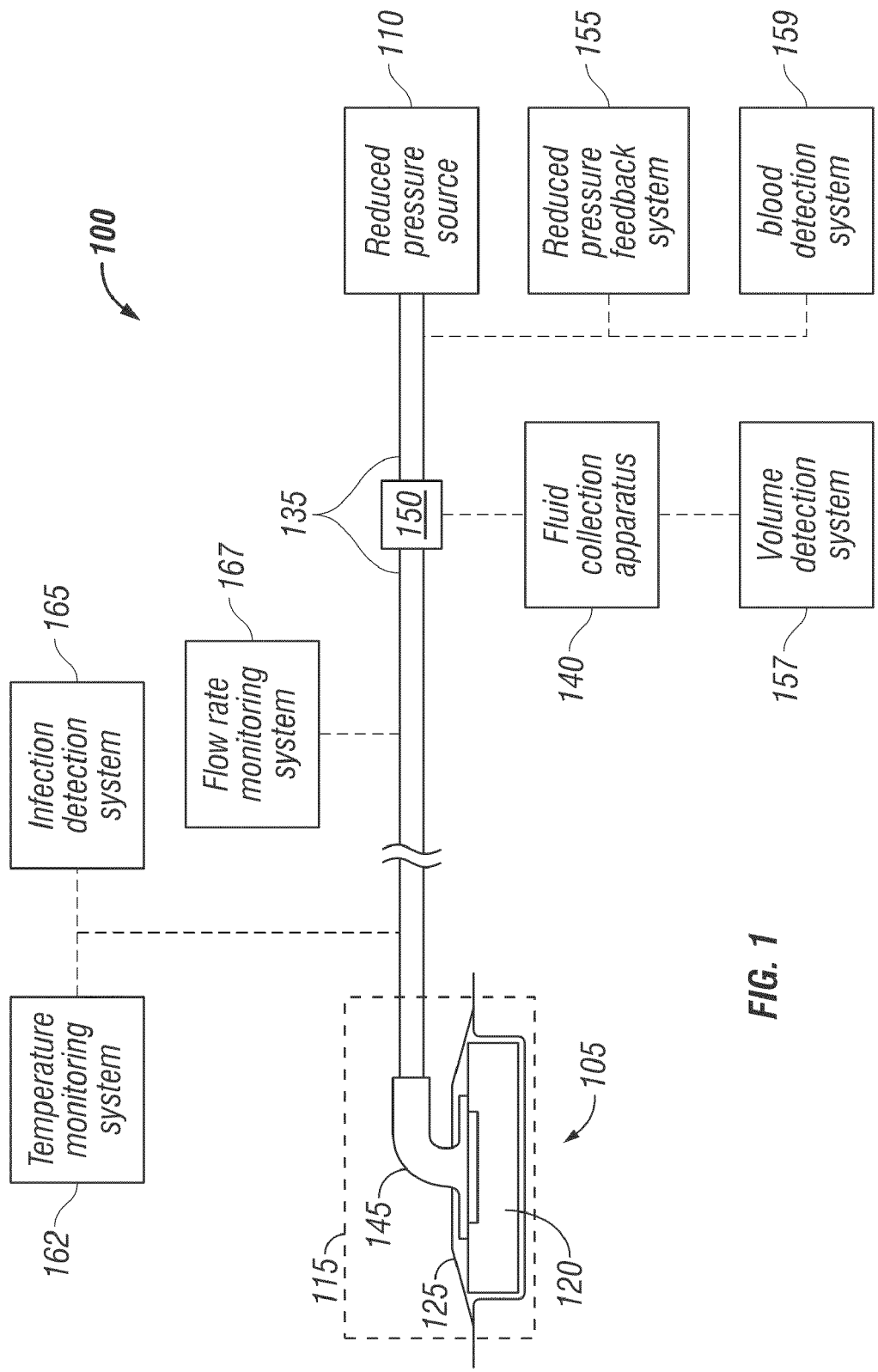
FIG. 1 is a block diagram of an apparatus for administering reduced pressure at a tissue site in accordance with an illustrative embodiment.

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

The illustrative embodiments described herein provide apparatus, systems, and methods for storing liquid removed from a tissue site. Reduced pressure generally refers to a pressure less than the ambient pressure at a tissue site that is being subjected to treatment. In most cases, this reduced pressure will be less than the atmospheric pressure of the location at which the patient is located. Although the terms "vacuum" and "negative pressure" may be used to describe the pressure applied to the tissue site, the actual pressure applied to the tissue site may be more than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure. Similarly, a reduced pressure that is "less" than a particular reduced pressure refers to an absolute pressure that is more than the absolute pressure that corresponds to the particular reduced pressure. Also, a reduced pressure that is "more" than a particular reduced pressure refers to an absolute pressure that is less than the absolute pressure that corresponds to the particular reduced pressure.

As used herein, the term "coupled" includes coupling via a separate object. The term "coupled" also includes "directly coupled," in which case the two objects touch each other in some way. The term "coupled" also encompasses two or more components that are continuous with one another by virtue of each of the components being formed from the same piece of material. Also, the term "coupled" includes chemical coupling, such as via a chemical bond. The term "coupled" may also include mechanical, thermal, or electrical coupling.

Currently, the use of reduced pressure treatment is not considered a viable or affordable option for low-severity wounds due to the manpower required to monitor and change system components, the requirement for trained medical personnel overseeing treatment, and the high cost of treatment. For example, the complexity of current reduced pressure treatment systems precludes a person with little or no specialized knowledge from administering such treatment to oneself or others. The size and power consumption characteristics of current reduced pressure treatment systems also limit the mobility of both the treatment system and the person to whom the treatment is being applied. Also, the high cost of current reduced pressure treatment systems can preclude the accessibility of such treatment systems to some users. Current reduced pressure treatment systems are also typically non-disposable after each treatment.

For example, current reduced pressure treatment systems require the use of a separate fluid container for the storage of exudate that is extracted from the tissue site. However, the inclusion of the added component of a fluid container increases the obtrusiveness, complexity, and weight of the reduced pressure treatment system, thereby increasing the discomfort and limiting the mobility of the patient.

Current reduced pressure treatment systems also lack user-friendly, non-obtrusive methods for indicating whether an adequate amount of reduced pressure is being applied to the tissue site by the reduced pressure treatment system. Therefore, persons with specialized knowledge are required in order to properly operate the reduced pressure treatment system, thereby increasing the cost and decreasing the accessibility of using the reduced pressure treatment system.

While reduced pressure could be applied to low-volume and low-exudating wounds using traditional reduced pressure treatment systems, a need exists for a more simple system that allows reduced pressure treatment to be administered without specialized medical training. A need further exists for a system that uses little power and is compact, allowing a user of the system to remain mobile and participate in normal day-to-day activities. Finally, a system is needed that is inexpensive so that the system can economically be used by a single patient and then disposed of following the end of treatment for that patient.

Turning now to FIG. 1, a reduced pressure treatment system 100, which applies reduced pressure to a tissue site 105, is shown according to an illustrative embodiment. Tissue site 105 may be the bodily tissue of any human, animal, or other organism, including bone tissue, adipose tissue, muscle tissue, dermal tissue, vascular tissue, connective tissue, cartilage, tendons, ligaments, or any other tissue. While tissue site 105 may include a wound, diseased tissue, or defective tissue, the tissue site may also be healthy tissue that is not wounded, diseased, or defective. The application of reduced pressure to tissue site 105 may be used to promote the drainage of exudate and other liquids from tissue site 105, as well as stimulate the growth of additional tissue. In the case in which tissue site 105 is a wound site, the growth of granulation tissue and removal of exudates and bacteria promotes healing of the wound. The application of reduced pressure to non-wounded or non-defective tissue, including healthy tissue, may be used to promote the growth of tissue that may be harvested and transplanted to another tissue location.

The reduced pressure that is applied to tissue site 105 is generated by a reduced pressure source 110. Reduced pressure source 110 may be any type of manually, mechanically, or electrically operated pump. Non-limiting examples of reduced pressure source 110 include devices that are driven by stored energy, and which are capable of producing a reduced pressure. Examples of such stored energy, reduced pressure sources include, without limitation, pumps driven by piezo electric energy, spring energy, solar energy, kinetic energy, energy stored in capacitors, combustion, and energy developed by Sterling or similar cycles. Other examples of reduced pressure source 110 include devices that are manually activated, such as bellows pumps, peristaltic pumps, diaphragm pumps, rotary vane pumps, linear piston pumps, pneumatic pumps, hydraulic pumps, hand pumps, foot pumps, and manual pumps such as those used with manually-activated spray bottles. Still other devices and processes that may be used or included in reduced pressure source 110 include syringes, lead screws, ratchets, clockwork-driven devices, pendulum-driven devices, manual generators, osmotic processes, thermal heating processes, and processes in which vacuum pressures are generated by condensation.

In another embodiment, reduced pressure source 110 may include a pump that is driven by a chemical reaction. A tablet, solution, spray, or other delivery mechanism may be delivered to the pump and used to initiate the chemical reaction. The heat generated by the chemical reaction may be used to drive the pump to produce the reduced pressure. In another embodiment, a pressurized gas cylinder such as a $CO_2$ cylinder is used to drive a pump to produce the reduced pressure. In still another embodiment, reduced pressure source 110 may be a battery-driven pump. Preferably, the pump uses low amounts of power and is capable of operating for an extended period of time on a single charge of the battery.

Reduced pressure source 110 provides reduced pressure to tissue site 105 via a dressing 115. Dressing 115 includes a manifold 120, which may be placed adjacent to or in contact with tissue site 105. Manifold 120 may be a biocompatible, porous material that is capable of being placed in contact with tissue site 105 and distributing reduced pressure to the tissue site 105. Manifold 120 may be made from foam, gauze, felted mat, or any other material suited to a particular biological application. Manifold 120 may include a plurality of flow channels or pathways to facilitate distribution of reduced pressure or fluids to or from tissue site 105.

In one embodiment, manifold 120 is a porous foam and includes a plurality of interconnected cells or pores that act as flow channels. The porous foam may be a polyurethane, open-cell, reticulated foam, such as GranuFoam manufactured by Kinetic Concepts, Inc. of San Antonio, Tex. If an open-cell foam is used, the porosity may vary, but is preferably about 400 to 600 microns. The flow channels allow fluid communication throughout the portion of manifold 120 having open cells. The cells and flow channels may be uniform in shape and size, or may include patterned or random variations in shape and size. Variations in shape and size of the cells of manifold result in variations in the flow channels, and such characteristics may be used to alter the flow characteristics of fluid through manifold 120.

Manifold 120 may also be constructed from bioresorbable materials that do not have to be removed from a patient's body following use of reduced pressure treatment system 100. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. Manifold 120 may further serve as a scaffold for new cell-growth, or a scaffold material may be used in conjunction with manifold 120 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. In one example, the scaffold material has a high void-fraction (i.e. a high content of air).

Dressing 115 also includes a sealing member 125. Manifold 120 may be secured to tissue site 105 using sealing member 125. Sealing member 125 may be a cover that is used to secure manifold 120 at tissue site 105. While sealing member 125 may be impermeable or semi-permeable, in one example sealing member 125 is capable of maintaining a reduced pressure at tissue site 105 after installation of the sealing member 125 over manifold 120. Sealing member 125 may be a drape or film made from a silicone based compound, acrylic, hydrogel or hydrogel-forming material, or any other biocompatible material that includes the impermeability or permeability characteristics desired for tissue site 105. Sealing member 125 may be formed of a hydrophobic material to prevent moisture absorption by the sealing member 125.

Instead of being provided in "sheet" form such as that of a drape, sealing member 125 may be provided in a pourable or sprayable form that is applied over the manifold 120 after placement of manifold 120 in contact with the tissue site 105. Similarly, sealing member 125 may include a device that is placed over manifold 120 and tissue site 105 to provide sealing functionality, including but not limited to a suction cup, a molded cast, and a bell jar.

In one embodiment, sealing member 125 is configured to provide a sealed connection with the tissue surrounding manifold 120 and tissue site 105. The sealed connection may be provided by an adhesive positioned along a perimeter of sealing member 125 or on any portion of sealing member 125 to secure sealing member 125 to manifold 120 or the tissue surrounding tissue site 105. The adhesive may be pre-positioned on sealing member 125 or may be sprayed or otherwise applied to sealing member 125 immediately prior to installing sealing member 125.

In some cases, sealing member 125 may not be required to seal tissue site 105. For example, tissue site 105 may be capable of being "self-sealed" to maintain reduced pressure. In the case of subcutaneous and deep tissue wounds, cavities, and fistulas, maintenance of reduced pressure at tissue site 105 may be possible without the use of sealing member 125. Since tissue often encases or surrounds these types of tissue sites, the tissue surrounding the tissue site acts effectively as a sealing member.

The reduced pressure generated by reduced pressure source 110 may be applied to tissue site 105 using a delivery tube 135. Delivery tube 135 may be any tube through which a gas, liquid, gel, or other fluid may flow. For example, exudate from tissue site 105 may flow through delivery tube 135. In FIG. 1, connector 150 couples delivery tube 135 to a fluid collection apparatus 140. However, delivery tube 135 may directly couple reduced pressure source 110 to dressing 115 without intervening connector 150 or fluid collection apparatus 140.

Delivery tube 135 may have any cross-sectional shape, such as a circle, oval, or polygon. In addition, delivery tube 135 may be made from any material, and may be either flexible or inflexible. Also, delivery tube 135 may include one or more paths or lumens through which fluid may flow. For example, delivery tube 135 may include two lumens. In this example, one lumen may be used for the passage of exudate from tissue site 105 to fluid collection apparatus 140. The other lumen may be used to deliver fluids, such as air, antibacterial agents, antiviral agents, cell-growth promotion agents, irrigation fluids, or other chemically active agents, to tissue site 105. The fluid source from which these fluids originate is not shown in FIG. 1.

In one embodiment, delivery tube 135 includes a delivery lumen and one or more collection lumens to collect exudate from tissue site 105. These lumens may also each include a filter to manage the flow of exudate through the lumens. Additional details regarding the inclusion of delivery lumens, collection lumens, and filters in delivery tube 135 are provided below in FIGS. 2-10.

In one embodiment, delivery tube 135 is coupled to manifold 120 via a connection member 145. Connection member 145 permits the passage of fluid from manifold 120 to delivery tube 135, and vice versa. For example, exudates collected from tissue site 105 using manifold 120 may enter delivery tube 135 via connection member 145. In another embodiment, reduced pressure treatment system 100 does not include connection member 145. In this embodiment, delivery tube 135 may be inserted directly into sealing member 125 or manifold 120 such that an end of delivery tube 135 is adjacent to or in contact with manifold 120.

Reduced pressure treatment system 100 includes fluid collection apparatus 140. Liquid, such as exudate, from tissue site 105 may flow through delivery tube 135 into fluid collection apparatus 140. Fluid collection apparatus 140 may be any device or cavity capable of containing a fluid, such as gases and liquids, as well as fluids that contain solids. For example, fluid collection apparatus 140 may contain exudates from tissue site 105. Delivery tube 135 may be directly connected to fluid collection apparatus 140, or may be coupled to fluid collection apparatus 140 via a connector, such as connector 150.

The fluid collection apparatus 140 may be a flexible or rigid canister, a bag, or pouch fluidly connected to manifold 120 by delivery tube 135. Fluid collection apparatus 140 may be a separate container or may be operably combined with reduced pressure source 110 to collect exudate and fluids. In an illustrative embodiment in which a manual pump, such as a bellows pump, is used as reduced pressure source 110, the variable-volume chamber that generates the reduced pressure may also serve as fluid collection apparatus 140, collecting fluid as the chamber expands. The fluid collection apparatus 140 may include a single chamber for collecting fluids, or alternatively may include multiple chambers. A desiccant or absorptive material may be disposed within fluid collection apparatus 140 to trap or control fluid once the fluid has been collected. In the absence of fluid collection apparatus 140, a method for controlling exudate and other fluids may be employed in which the fluids, especially those that are water soluble, are allowed to evaporate from manifold 120. In another embodiment, one or more collection lumens in delivery tube 135, which will be described below in FIG. 2-10, may be used in lieu of or in addition to fluid collection apparatus 140.

Reduced pressure treatment system 100 includes a reduced pressure feedback system 155 operably associated with the other components of reduced pressure treatment system 100 to provide information to a user of the reduced pressure treatment system 100 indicating a relative or absolute amount of pressure that is being delivered to the tissue site 105 or that is being generated by reduced pressure source 110. Examples of feedback systems include, without limitation, pop valves that activate when the reduced pressure rises above a selected value and deflection pop valves. Additional details regarding feedback systems that include pop valves and, in particular, movable indicators that respond to reduced pressure in delivery tube 135, are provided below with respect to FIGS. 15-19.

Other non-limiting examples of feedback systems include low power electronic indicators powered by miniature cells, dial indicators that indicate specific pressure values that are being applied to the tissue site, polymers with various deflection characteristics, and films that move relative to one another to produce visual identifiers indicating the relative or absolute pressure values being generated by the reduced pressure source 110. An example of a "film" based system may include a yellow film anchored to a first part of the reduced pressure source 110 that is capable of movement relative to a blue film anchored to a second part. When the first and second parts are moved relative to one another to apply a reduced pressure, the yellow and blue films overlap to create a green indicator. As the pressure increases and the films move away from one another, the loss of the green color indicates that the pressure has increased (i.e. more reduced pressure needs to be applied).

Reduced pressure treatment system 100 may further include a volume detection system 157 to detect the amount of fluid present in fluid collection apparatus 140, a blood detection system 159 to detect the presence of blood in exudate drawn from tissue site 105, a temperature monitoring system 162 to monitor the temperature of tissue site 105, an infection detection system 165 to detect the presence of infection at tissue site 105, and/or a flow rate monitoring system 167 to monitor the flow rate of fluids drawn from tissue site 105. Infection detection system 165 may include a foam or other substance that changes color in the presence of bacteria. The foam or other substance may be operably associated with manifold 120 or delivery tube 135 such that the color changing material is exposed to exudate from tissue site 105. In addition to the above-mentioned components and systems, reduced pressure treatment system 100 may include valves, regulators, switches, and other electrical, mechanical, and fluid components to facilitate administration of reduced pressure treatment to tissue site 105.

Figure 2:
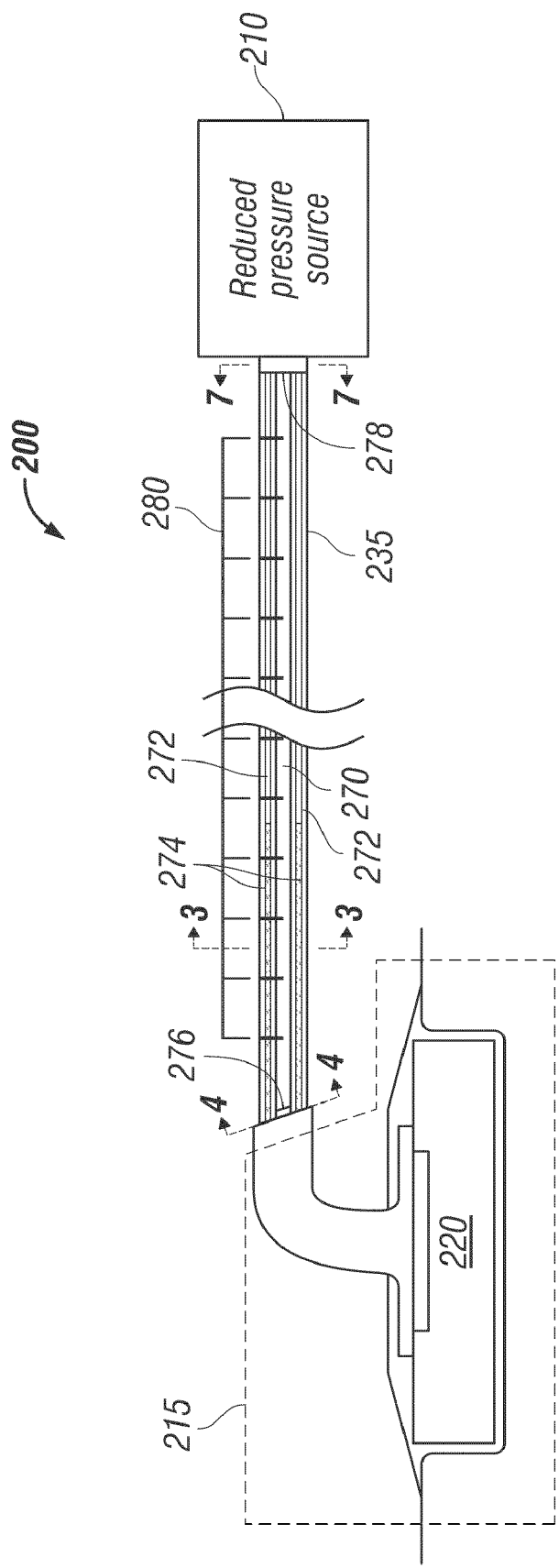
FIG. 2 is a block diagram of an apparatus for administering reduced pressure at a tissue site in accordance with an illustrative embodiment.

Turning now to FIG. 2, reduced pressure treatment system 200, which is a non-limiting example of reduced pressure treatment system 100 in FIG. 1, is shown according to an illustrative embodiment. In one embodiment, fluid collection apparatus 140 in FIG. 1 is tube 235 fluidly connected between the dressing 215 and the reduced pressure source 210. Dressing 215 and reduced pressure source 210 are non-limiting examples of dressing 115 and reduced pressure source 110 in FIG. 1, respectively.

Tube 235 includes a plurality of lumens. In particular, tube 235 includes a delivery lumen 270 and a plurality of collection lumens 272. Although FIG. 2 shows tube 235 as having a single delivery lumen 270 and two collection lumens 272, tube 235 may have any number of delivery and collection lumens. For example, multiple delivery lumens and a single collection lumen may be included in tube 235.

All of the plurality of lumens in tube 235, including delivery lumen 270 and plurality of collection lumens 272, are fluidly connected to reduced pressure source 210 such that all are exposed to reduced pressure. Thus, reduced pressure generated by reduced pressure source 210 may be transmitted through each of the plurality of lumens in tube 235 to tissue site 205 via dressing 215. In one embodiment, reduced pressure source 210 applies reduced pressure to tissue site 205 through delivery lumen 270 and plurality of collection lumens 272 such that the plurality of collection lumens 272 receives a fluid 274, such as a liquid or a liquid containing solids, from tissue site 205. In one example, fluid 274 is exudate from tissue site 205. Plurality of collection lumens 272 may store fluid 274 received from tissue site 205. Thus, the need for a separate fluid collection apparatus, such as fluid collection apparatus 140 in FIG. 1, is eliminated.

Reduced pressure treatment system 200 may include at least one filter coupled to tube 235. In particular, tube 235 includes a delivery lumen filter 276 and collection lumen filter 278. Delivery lumen filter 276 and collection lumen filter 278 prevents fluid 274 from tissue site 205 from passing or flowing past the one or more locations at which the filters are located. Delivery lumen filter 276 and collection lumen filter 278 may be any type of filter capable of preventing the flow of fluid 274, such as a hydrophobic filter, a hydrophilic filter, and a mechanical valve. In the example in which delivery lumen filter 276 or collection lumen filter 278 is a mechanical valve, a one-way valve, such as a duck-bill valve, may be used.

Delivery lumen filter 276 is coupled to the end of tube 235 that is adjacent to tissue site 205 and dressing 215. As used herein, "adjacent" means at or near another object. In one example, a first object may be adjacent to a particular object if the first object is nearer to the particular object than a second object. Thus, a first end of tube 235 may be adjacent to tissue site 205 if the first end of the tube is nearer to tissue site 205 than a second end of the tube. Delivery lumen filter 276 restrains or prevents fluid 274 from entering delivery lumen 270 through one or more components of dressing 215. Thus, reduced pressure may continually be applied via delivery lumen 270 unobstructed by fluid 274, even as fluid 274 is collected into plurality of collection lumens 272.

Although FIG. 2 shows delivery lumen filter 276 as preventing any fluid 274 from entering delivery lumen 270, delivery lumen filter 276 may also be placed so as to prevent fluid 274 from passing a particular point along delivery lumen 270. For example, delivery lumen filter 276 may be placed inside of delivery lumen 270 at a particular distance away from an end of tube 235 such that fluid 274 is allowed to enter a portion of delivery lumen 270 unobstructed by delivery lumen filter 276. Additional details regarding the placement and coupling of delivery lumen filter 276 is provided in FIGS. 4-6 below.

Collection lumen filter 278 is coupled to the end of tube 235 that is adjacent to reduced pressure source 210. Collection lumen filter 278 prevents fluid 274 from entering reduced pressure source 210 or from exiting plurality of collection lumens 272. Due to the location of collection lumen filter 278, plurality of collection lumens 272 between the dressing 215 and collection lumen filter 278 are reservoirs capable of receiving exudate and other fluids from tissue site 205. Since plurality of collection lumens 272 are influenced by reduced pressure source 210, fluids are drawn from tissue site 205 through manifold 220, which is adjacent to tissue site 205, into plurality of collection lumens 272. The volume of space available for fluid depends upon the diameter and number of collection lumens in plurality of collection lumens 272, as well as the length of each collection lumen between dressing 215 and collection lumen filter 278. For example, plurality of collection lumens 272 may be capable of holding approximately 30-60 cubic centimeters of fluid 274. However, the aforementioned physical parameters of plurality of collection lumens 272 may be adjusted based on the particular implementation such that plurality of collection lumens 272 may store any amount of fluid 274.

As plurality of collection lumens 272 fill with fluid, plurality of collection lumens 272 continue to be capable of transmitting reduced pressure from reduced pressure source 210. When plurality of collection lumens 272 are completely full of fluid 274 between dressing 215 and collection lumen filter 278, reduced pressure may no longer be capable of being transmitted through plurality of collection lumens 272. However, delivery lumen 270 continues to transmit reduced pressure even after the plurality of collection lumens 272 is full.

Although collection lumen filter 278 is shown as being coupled to the end of tube 235 that is adjacent to reduced pressure source 210, collection lumen filter 278 may be located anywhere along tube 235. For example, collection lumen filter 278 may be located at a midpoint along the length of tube 235. In this example, plurality of collection lumens 272 may fill with fluid 274 until fluid 274 becomes obstructed by collection lumen filter 278 at the midpoint of tube 235. Thus, collection lumen filter 278 prevents fluid 274 from passing the midpoint of tube 235 along plurality of collection lumens 272. In this example, only a portion of the space defined by plurality of collection lumens 272 may fill with fluid 274.

In another example, reduced pressure treatment system 200 may include multiple collection lumen filters. In this example, each collection lumen filter may be located at a different location along each collection lumen in plurality of collection lumens 272. Thus, each collection lumen in plurality of collection lumens 272 may have a different fluid capacity.

Because reduced pressure treatment system 200 may be used to treat low-exudating tissue sites, the smaller fluid collection volume provided by plurality of collection lumens 272 (as opposed to a dedicated canister) has little or no effect on the ability of reduced pressure treatment system 200 to provide treatment for an extended period of time. The compact nature of a fluid collection apparatus that is integrated into a reduced pressure delivery tube minimizes patient discomfort and maximizes patient mobility. During treatment, when plurality of collection lumens 272 becomes completely full of fluid 274, tube 235 may be easily replaced with a new tube.

To minimize the risk of spilling fluid during tubing changes, or having fluid backflow into manifold 220 during treatment, plurality of collection lumens 272 may be partially filled or packed with desiccants, absorptive materials, or other trapping agents. Non-limiting embodiments of delivery tubes having such absorbent and/or trapping characteristics are shown in FIGS. 10-14 below.

In FIG. 2, the portion of plurality of collection lumens 272 that contains fluid 274 is shaded to show that fluid 274 is visible to a user of reduced pressure treatment system 200. Tube 235 may include at least one substantially transparent tube portion through which fluid 274 may be visible. For example, the one or more substantially transparent tube portions may be a window on tube 235 made from a transparent material. Each of these windows may extend across portions of tube 235 that are adjacent to each respective collection lumen 272.

In another example, the material from which tube 235 is made may be a transparent material. Thus, fluid 274 may be visible due to the total transparency of tube 235. Because fluid 274 from tissue site 205, such as exudate, may have a darkened color, fluid levels within plurality of collection lumens 272 may be easily ascertainable by a user.

Tube 235 also includes demarcations 280. Demarcations 280 indicate an amount of fluid 274 in plurality of collection lumens 272. In the example in which tube 235 includes one or more substantially transparent tube portions, such as transparent windows, demarcations 280 may be included along each the windows. Each of demarcations 280 may correspond to a specific volume or amount of fluid 274. For example, the first of demarcations 280 may be labeled "5 cc" and each demarcation thereafter may be labeled in 5 cubic centimeters increments. The particular incremented used may depend on the implementation.

Figure 3:
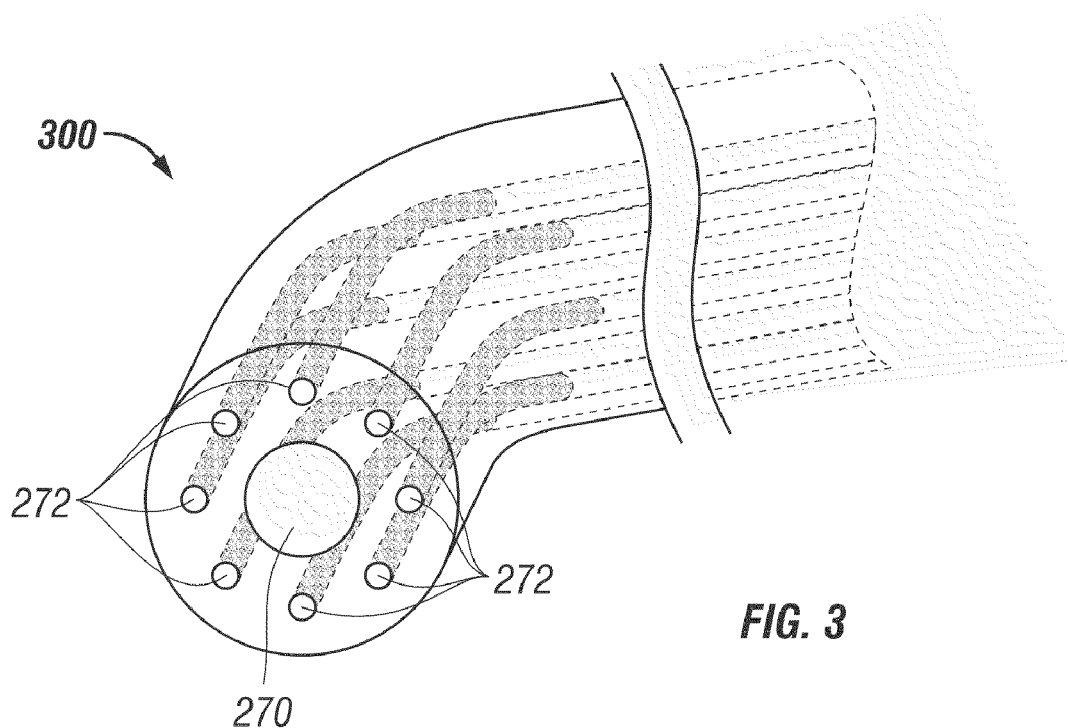
FIG. 3 is a cross-sectional view of components of an apparatus for administering reduced pressure at a tissue site in accordance with an illustrative embodiment.

Turning now to FIG. 3, a cross-sectional view of tube 300 is shown from the perspective of cross-sectional indicator 3 in FIG. 2. As shown in FIG. 3, delivery lumen 270 has a larger cross-section than each of collection lumens 272. However, in one example, the cross-section of delivery lumen 270 may be the same or smaller than the cross-section of each of collection lumens 272. Delivery lumen 270 and collection lumens 272 also have a circular cross-section shape. However, delivery lumen 270 and collection lumens 272 may have any cross-sectional shape, such as an oval, polygonal, or irregular cross-sectional shape.

Each of collection lumens 272 is shown as equidistant from delivery lumen 270 such that collection lumens 272 surround delivery lumen 270 in a circular pattern. However, delivery lumen 270 and collection lumens 272 may have any spatial configuration relative to one another, including configurations in which each of collection lumens 272 are a different distance from delivery lumen 270. In addition, tube 300 may include two or more delivery lumens, such as delivery lumen 270. Any number of collection lumens 272 may also be included in tube 300. In one example, the number of delivery lumens in tube 300 exceeds the number of collection lumens.

Delivery lumen 270 is also shown to be located along the longitudinal center of tube 300. However, delivery lumen 270 may be located along any longitudinal axis that traverses the length of tube 300. In one example, delivery lumen 270 and collection lumens 272 may be defined by walls that longitudinally extend through the length of tube 300. In this example, two or more intersecting walls may define quadrants, any of which may be a delivery lumen or collection lumen.

Figure 4:
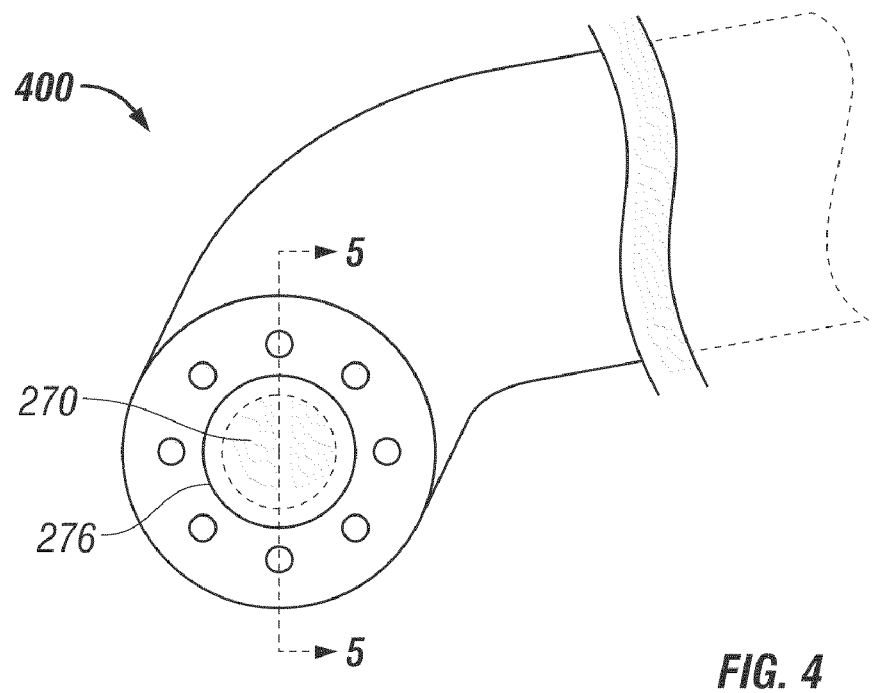
FIG. 4 is a cross-sectional view of components of an apparatus for administering reduced pressure at a tissue site in accordance with an illustrative embodiment.

Turning now to FIG. 4, a cross-sectional view of tube 400 is shown from the perspective of cross-sectional indicator 4 in FIG. 2. Tube 400 includes delivery lumen filter 276, which is coupled to tube 400 at the opening of delivery lumen 270. Delivery lumen filter 276 may have the same or slightly larger cross-section than delivery lumen 270 to ensure the delivery lumen filter 276 can prevent fluid from entering delivery lumen 270. Delivery lumen filter 276 may be coupled to the end of tube 400 using any method. For example, delivery lumen filter 276 may be welded, screwed, glued, bolted, air-lock sealed, snapped, or pressed onto the end of tube 400.

Figure 5:
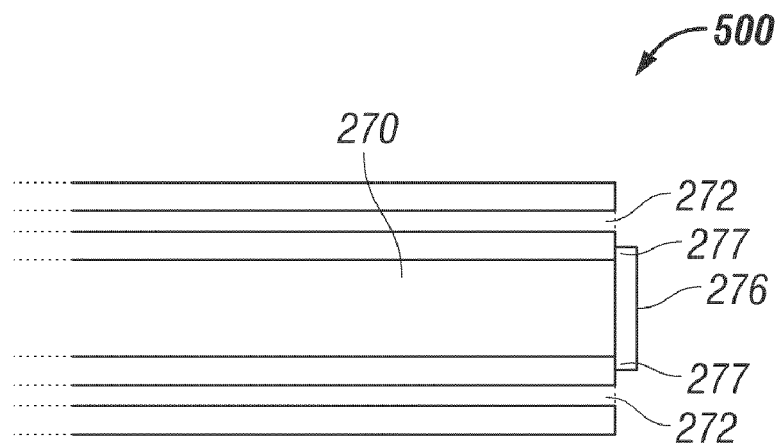
FIG. 5 is a cross-sectional view of components of an apparatus for administering reduced pressure at a tissue site in accordance with an illustrative embodiment.

Turning now to FIG. 5, a cross-sectional view of tube 500 is shown from the perspective of cross-sectional indicator 5 in FIG. 4. FIG. 5 shows the opening of delivery lumen 270 obstructed by delivery lumen filter 276 such that fluid from a tissue site cannot enter delivery lumen 270. In particular, delivery lumen filter 276 is shown to be located just outside of delivery lumen 270 such that delivery lumen filter 276 overhangs the diameter of delivery lumen 270 at overhanging portions 277. Delivery lumen filter 276 may have any thickness sufficient to prevent the flow of fluid into delivery lumen 270. The openings of collection lumens 272 are unobstructed by delivery lumen filter 276 such that fluid may be received and collected by collection lumens 272.

Figure 6:
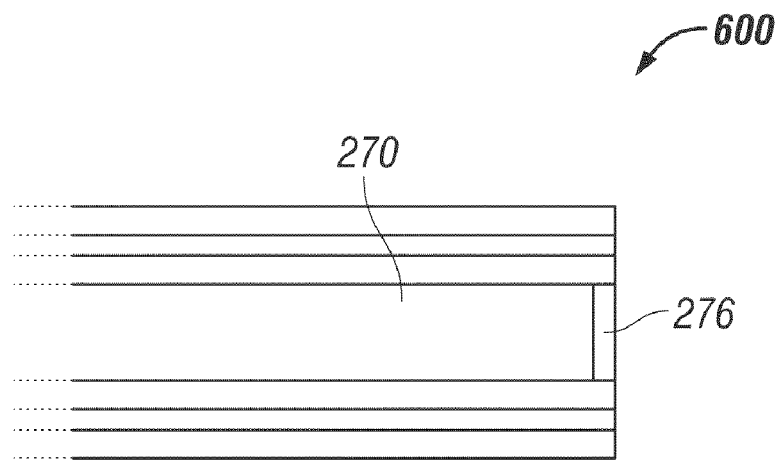
FIG. 6 is a cross-sectional view of components of an apparatus for administering reduced pressure at a tissue site in accordance with an illustrative embodiment.

Turning now to FIG. 6, a cross-sectional view of tube 600 is shown in which delivery lumen filter 276 has a different size and configuration as delivery lumen filter 276 in FIG. 5. In particular, delivery lumen filter 276 has a diameter approximately equal to the diameter of delivery lumen 270 such that delivery lumen filter 276 fits into the space defined by delivery lumen 270. Although delivery lumen filter 276 is shown to be positioned at the end of delivery lumen 270, delivery lumen filter 276 may be located anywhere along the length of delivery lumen 270. In this example, delivery lumen filter 276 prevents fluid from a tissue site from passing the location at which delivery lumen filter 276 is located along delivery lumen 270.

Figure 7:
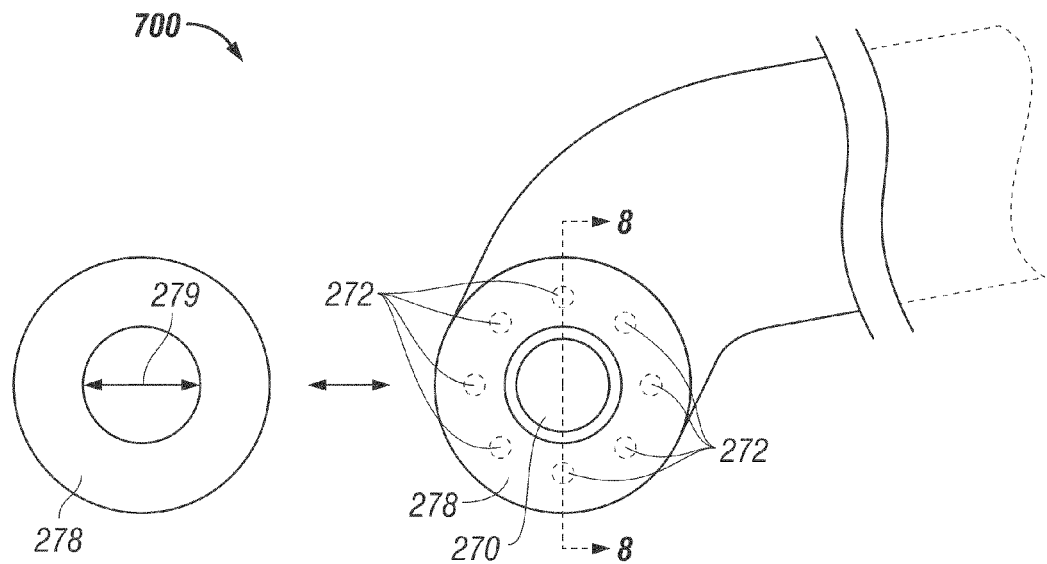
FIG. 7 is a cross-sectional view of components of an apparatus for administering reduced pressure at a tissue site in accordance with an illustrative embodiment.

Turning now to FIG. 7, a cross-sectional view of tube 700 is shown from the perspective of cross-sectional indicator 7 in FIG. 2. Tube 700 includes collection lumen filter 278. Collection lumen filter 278 is shown to be coupled to an end of tube 700. Collection lumen filter 278 is also shown as decoupled from the end of tube 700 to better show the shape of collection lumen filter. Collection lumen filter 278 is a disk having an aperture 279. When coupled onto the end of tube 700, collection lumen filter 278 covers collection lumens 272 but does not cover delivery lumen 270, as aperture 279 is located at the opening of delivery lumen 270. Thus, collection lumen filter 278 may prevent fluid that has been collected by collection lumen filter 278 from exiting collection lumens 272 and entering a reduced pressure source, such as reduced pressure source 210 in FIG. 2. However, reduced pressure may still be applied through collection lumen filter 278 such that collection lumens 272 may transmit reduced pressure to a tissue site. Although collection lumen filter 278 is shown to have an "O" shape, collection lumen filter 278 may have any shape capable of preventing fluid from exiting one or more of collection lumens 272. For example, the collection lumen filter 278 may be a disc that has no central hole, as gas may still be allowed to exit delivery lumen 270.

Collection lumen filter 278 may be coupled to the end of tube 700 using any method. For example, collection lumen filter 278 may be welded, screwed, glued, bolted, air-lock sealed, snapped, or pressed onto the end of tube 700.

Figure 8:
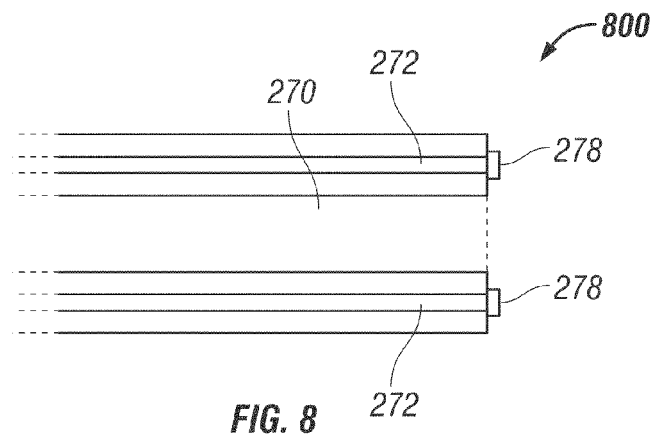
FIG. 8 is a cross-sectional view of components of an apparatus for administering reduced pressure at a tissue site in accordance with an illustrative embodiment.

Turning now to FIG. 8, a cross-sectional view of tube 800 is shown from the perspective of cross-sectional indicator 8 in FIG. 7. FIG. 8 shows the opening of collection lumens 272 obstructed by collection lumen filter 278 such that fluid from a tissue site cannot exit collection lumens 272 or enter a reduced pressure source. In particular, collection lumen filter 278 is shown to be located just outside collection lumens 272 such that collection lumen filter 278 overhangs each diameter of each collection lumens 272. Collection lumen filter 278 may have any thickness sufficient to prevent the flow of fluid out of collection lumen filter 278. The opening of delivery lumen 270 is unobstructed by collection lumen filter 278 such that no hindrance exists between the opening of delivery lumen 270 and a reduced pressure source.

Figure 9:
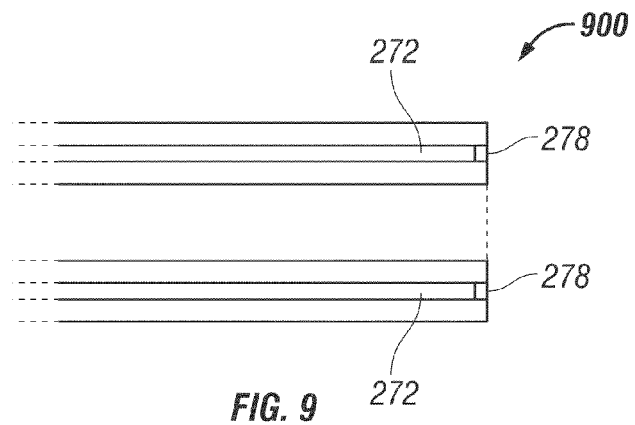
FIG. 9 is a cross-sectional view of components of an apparatus for administering reduced pressure at a tissue site in accordance with an illustrative embodiment.

Turning now to FIG. 9, a cross-sectional view of tube 900 is shown in which collection lumen filter 278 has a different size and configuration as collection lumen filter 278 in FIG. 8. In particular, collection lumen filter 278 includes multiple collection lumen filters, each of which are located inside the space defined by collection lumens 272. The diameter of each collection lumen filter 278 is approximately equal to the diameter of each collection lumen 272 such that collection lumen filters 278 fit into collection lumens 272. In this example, each of collection lumen filters may be mechanical valves that prevent the flow of liquid, such as exudate, but do not prevent the flow of gas, thereby allowing the flow of reduced pressure across collection lumen filters 278. Although collection lumen filters 278 are shown to be positioned at the ends of each collection lumen 272, collection lumen filters 278 may be located anywhere along the length of collection lumens 272, thereby defining a fluid capacity for each collection lumen 272. Each one of collection lumen filter 278 may also be located at different locations along each respective collection lumen 272 such that each collection lumen 272 has a different fluid capacity.

Figure 10:
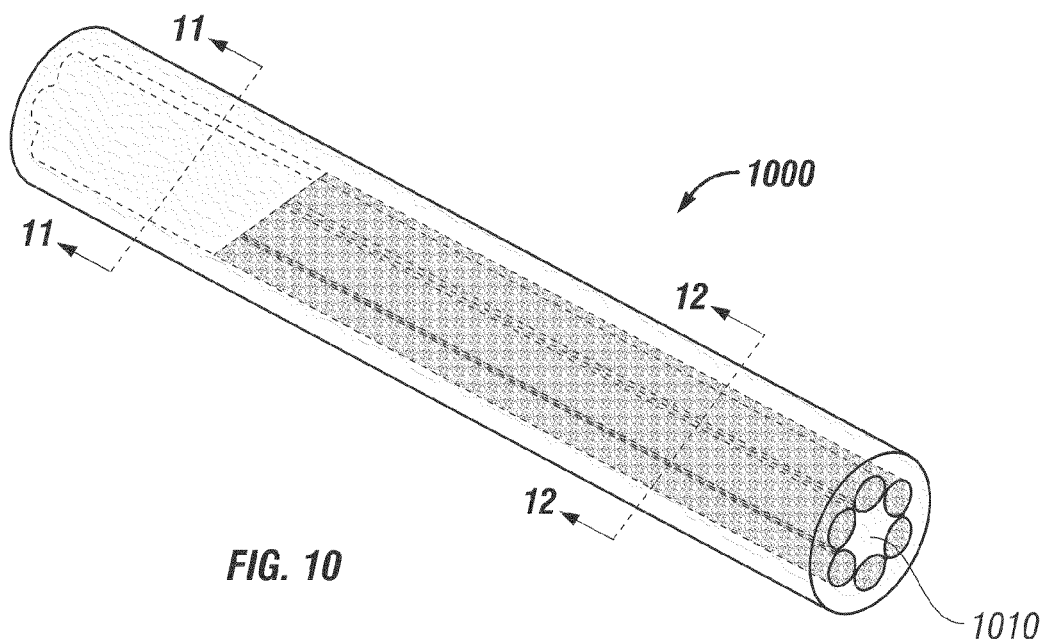
FIG. 10 is a perspective view with a portion broken away of a delivery tube storing liquid from a tissue site in accordance with an illustrative embodiment.
Figure 11:
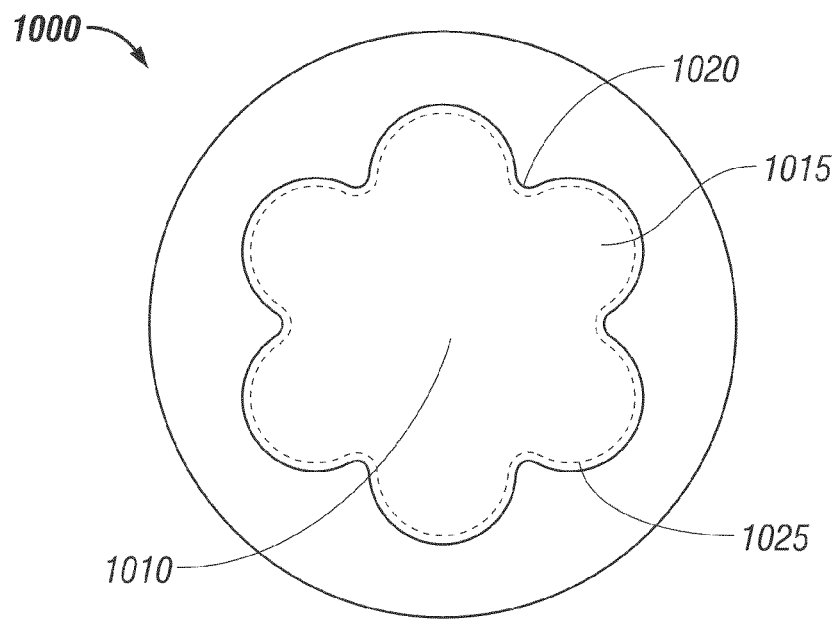
FIG. 11 is a cross-sectional view of a delivery tube storing liquid from a tissue site in accordance with an illustrative embodiment.

Turning now to FIGS. 10 and 11, a delivery tube 1000 is shown according to an illustrative embodiment. In particular, FIG. 10 shows a perspective view with a portion broken away of the delivery tube 1000. FIG. 11 shows a cross-sectional view of the delivery tube 1000 taken along line 11-11 in FIG. 10. Delivery tube 1000 is another non-limiting embodiment of delivery tube 135 in FIG. 1 or tube 235 in FIG. 2. Delivery tube 1000, which includes lumen 1010, is operable to transmit reduced pressure from a reduced pressure source, such as reduced pressure source 110 in FIG. 1, to a tissue site, such as tissue site 105 in FIG. 1. Delivery tube 1000 may also be operable to receive liquid from a tissue site. In particular, the reduced pressure transmitted through delivery tube 1000 may cause liquid from a tissue site to be drawn into the lumen 1010. In one embodiment, the reduced pressure is also transmitted through a dressing, such as dressing 115 in FIG. 1, such that the liquid enters delivery tube 1000 via components of the dressing, such as manifold 120 and connection member 145 in FIG. 1. Although FIGS. 10 and 11 show delivery tube 1000 to have a single lumen 1010, delivery tube 1000 may include any number of lumens, such as lumen 1010.

Lumen 1010 includes recesses 1015, which may form elongated indentations on the inner surface of the lumen 1010. Recesses 1015 may extend along at least a portion of the length of delivery tube 1000. In another embodiment, recesses 1015 extend along an entire length of delivery tube 1000. A wall of each of recesses 1015 may have a substantially semi-circular cross-sectional shape. However, the cross-sectional shape of any of the walls of recesses 1015 may have any shape, such as a portion of a polygon, ellipse, or irregular shape. In one example, the cross-sectional shape of any of the walls of recesses 1015 may be varied to adjust the absorbent capacity of delivery tube 1000.

Lumen 1010 includes ribs 1020. Recesses 1015 are separated from one another by at least one of ribs 1020. Although FIGS. 10 and 11 show lumen 1010 to have six recesses 1015 and six ribs 1020, lumen 1010 may have any number of lumens and ribs. For example, the number of recesses may be altered to adjust fluid storage capacity or absorbent characteristics of delivery tube 1000.

Delivery tube 1000 may also include absorbent material 1025. The absorbent material 1025 is disposed in lumen 1010. Absorbent material 1025 is operable to absorb and store liquid, such as exudate, from a tissue site. Non-limiting examples of absorbent material include super absorbent fiber/particulates, hydrofiber, sodium carboxymethyl cellulose, and alginates. Absorbent material 1025 may at least partially cover an inner surface of lumen 1010. In another embodiment, absorbent material 1025 covers an entire inner surface of lumen 1010.

In another embodiment, absorbent material 1025 may be disposed in all or a portion of recesses 1015. For example, absorbent material 1025 may cover the inner surface of each of recesses 1015. In this embodiment, absorbent material 1025 may also cover ribs 1020. The amount of absorbent material 1025 that is used to cover all or a portion of the inner surface of the lumen 1010, including the inner surface of each of recesses 1015, may be varied to increase or decrease the absorbent capacity of delivery tube 1000.

Figure 12:
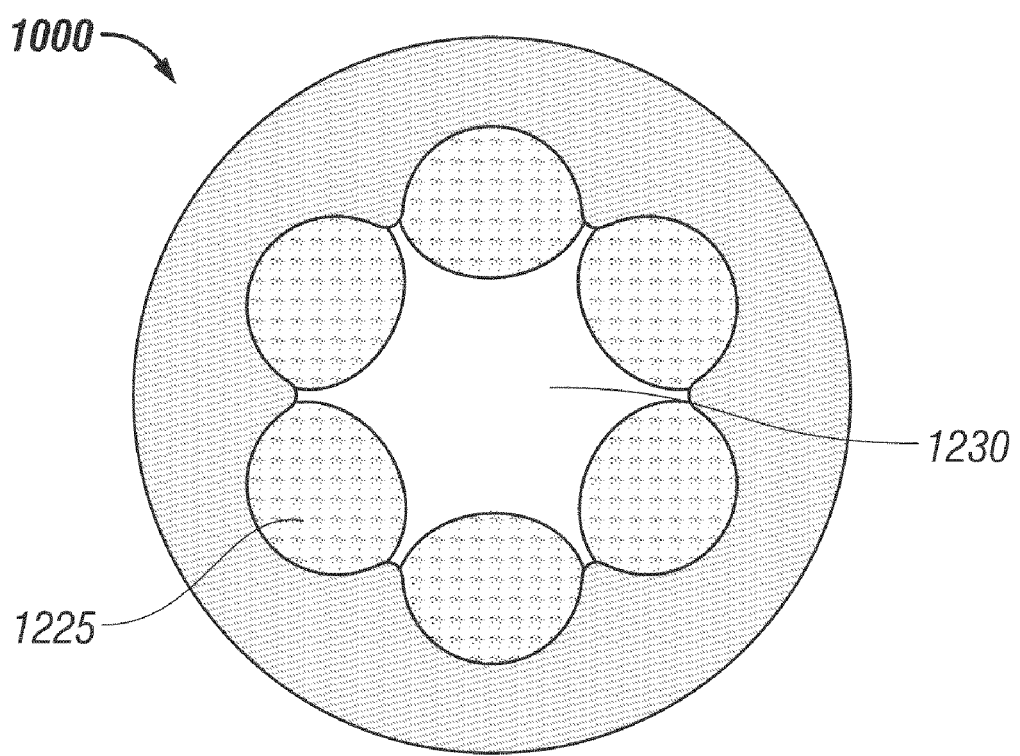
FIG. 12 is a cross-sectional view of a delivery tube storing liquid from a tissue site in accordance with an illustrative embodiment.

Turning now to FIG. 12, a cross-sectional view of the delivery tube 1000 taken along line 12-12 in FIG. 10 is shown. In particular, FIG. 12 shows a portion of delivery tube 1000 in which absorbent material 1025 has been saturated with liquid from the tissue site to form saturated absorbent material 1225. Saturated absorbent material 1225 may store liquid, such as exudate, from a tissue site. Delivery tube 1000 includes central reduced pressure passage 1230, which remains even when the absorbent material is saturated with liquid from a tissue site. Thus, delivery tube 1000 may continue to transmit reduced pressure when all or a portion of the absorbent material in lumen 1010 is saturated with liquid.

Figure 13:
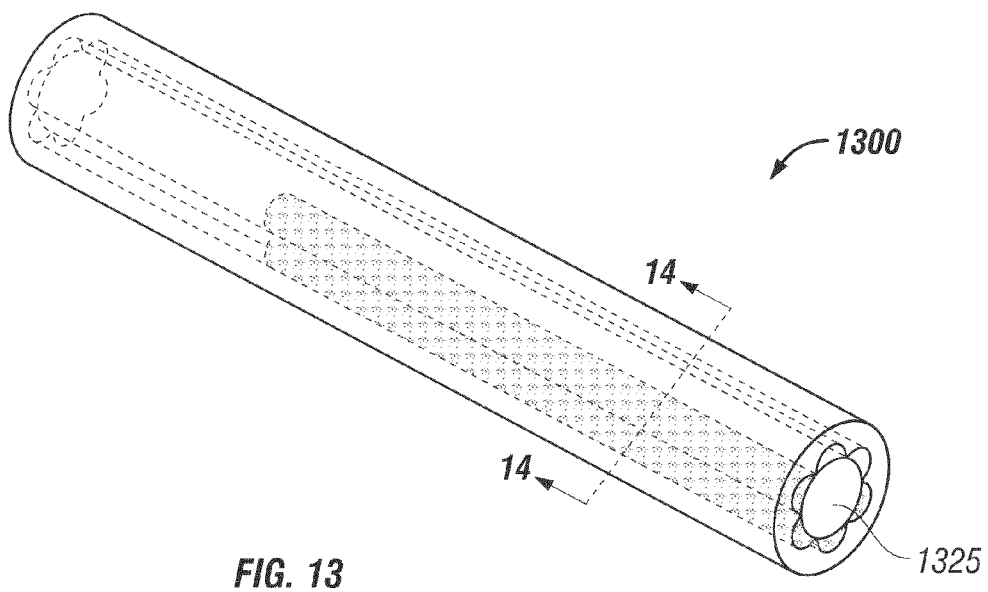
FIG. 13 is a perspective view with a portion broken away of a delivery tube storing liquid from a tissue site in accordance with an illustrative embodiment.
Figure 14:
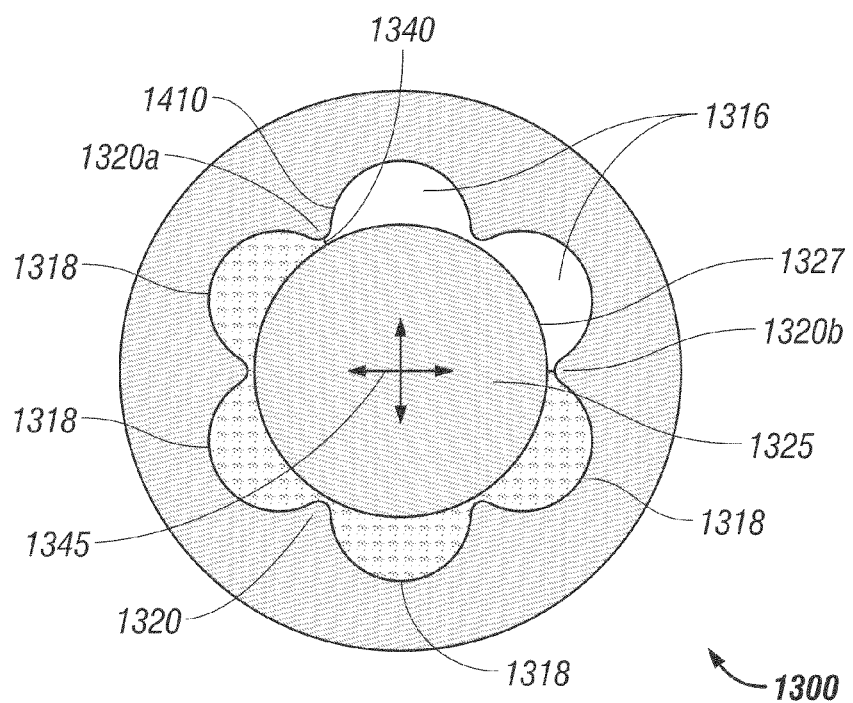
FIG. 14 is a cross-sectional view of a delivery tube storing liquid from a tissue site in accordance with an illustrative embodiment.

Turning now to FIGS. 13 and 14, a delivery tube 1300 is shown according to an illustrative embodiment. In particular, FIG. 13 shows a perspective view with a portion broken away of delivery tube 1300. FIG. 14 shows a cross-sectional view of delivery tube 1300 taken along line 14-14 in FIG. 13. Delivery tube 1300 is another non-limiting embodiment of delivery tube 135 in FIG. 1 or tube 235 in FIG. 2.

Delivery tube 1300 includes lumen 1410, which is a non-limiting example of lumen 1010 in FIG. 10. Lumen 1410 includes absorbent core 1325. Absorbent core 1325 is operable to absorb liquid from a tissue site. In one embodiment, absorbent core 1325 expands as absorbent core 1325 absorbs liquid from a tissue site. In one example, absorbent core 1325 may be made from the same or similar material as absorbent material 1025 in FIGS. 10 and 11. In another example, absorbent core 1325 may be a foam material that includes an absorbent material, including the same or similar material as absorbent material 1025 in FIGS. 10 and 11. The absorbent core 1325 may also be made from water soluble polymers such as poly vinyl alcohol.

When delivery tube 1300 is substantially straight, absorbent core 1325 may have a substantially cylindrical shape. Absorbent core 1325 may also have a substantially circular cross-section shape, as shown in FIG. 14. Because delivery tube 1300 and absorbent core 1325 may be flexible, the substantially cylindrical absorbent core 1325 may be bent into various orientations.

Lumen 1410 includes recesses 1316 and 1318, each of which is a non-limiting example of recesses 1015 in FIGS. 10 and 11. In the example of FIGS. 13 and 14, liquid, such as exudate, is contained in recesses 1318. Conversely, no liquid is contained in recesses 1316. In one embodiment, each of recesses 1316 and 1318 may be in fluid communication with one another via a gap, such as gap 1340. In this embodiment, the liquid may flow into any of recesses 1316 and 1318. The presence of recesses 1316 and 1318 may help to ensure that an open passage is maintained through which reduced pressure may be transmitted. Such an open passage may be maintained when delivery tube 1300 is bent or flexed. Other cross-sectional shapes of lumen 1410 may also be used to ensure such an open passage.

In one embodiment, recesses 1316 are reduced pressure delivery recesses for delivering reduced pressure from a reduced pressure source; in this embodiment, recesses 1318 may be collection recesses for storing liquid from a tissue site. Any number of the total number of recesses may be either reduced pressure recesses or collection recesses. Also, in one embodiment, either or both of recesses 1316 and 1318 may be coated with an absorbent material, such as absorbent material 1025 in FIG. 11. Outer surface 1327 of absorbent core 1325 may also be coated with an absorbent material.

In another embodiment, fluid communication between each of recesses 1316 and 1318 may be prevented by direct contact between outer surface 1327 of absorbent core 1325 and ribs 1320. In this embodiment, the liquid may be prevented from flowing from one recess into another, such as when absorbent core 1325 has expanded after absorbing the liquid. In another embodiment, a wall, membrane, or other member may connect outer surface 1327 of absorbent core 1325 to each of ribs 1320a and 1320b such that liquid is unable to pass into recesses 1316 from recesses 1318. In this embodiment, recesses 1316 are reduced pressure delivery recesses, and may always transmit reduced pressure regardless of the amount of liquid absorbed by delivery tube 1300. Also in this embodiment, a filter, such as delivery lumen filter 276 in FIG. 2, may be placed at an end of delivery tube 1300 that is adjacent to a tissue site such that liquid from the tissue site cannot enter recesses 1316. For example, the filter may cover an entrance to recesses 1316 on the end of delivery tube 1300 that is adjacent to the tissue site.

In another embodiment, absorbent core 1325 may be capable of absorbing liquid that is drawn into delivery tube 1300 such that no liquid need be contained in any of recesses 1316 and 1318. In this embodiment, liquid may begin to collect in any of recesses 1316 and 1318 when absorbent core 1325 becomes saturated with liquid. Also in this embodiment, all of recesses 1316 and 1318 may transmit reduced pressure to a tissue site while absorbent core 1325 still has absorbent capacity. In another embodiment, lumen 1410 has no recesses at all, and may have a substantially circular cross-sectional shape.

Absorbent core 1325 may be able to move within lumen 1410. For example, absorbent core 1325 may be able to move in the directions indicated by multi-directional arrows 1345. Thus, in the case in which each of recesses 1316 and 1318 are in fluid communication with one another, the movement of absorbent core 1325, such as when delivery tube 1300 is being flexed, may facilitate the movement of liquid between recesses, and may also facilitate the transmission of reduced pressure.

In one embodiment, a method for storing liquid from a tissue site may include placing a delivery tube, as described in any of the illustrative embodiments, in fluid communication with a tissue site. The method may also include supplying a reduced pressure to the at least one lumen in the delivery tube such that liquid from the tissue site is drawn into the at least one lumen. The method may also include absorbing the liquid from the tissue site using an absorbent material within the at least one lumen such that the liquid from the tissue site is stored in the at least one lumen. In one embodiment, the method may also include applying a manifold, such as manifold 120 in FIG. 1, to the tissue site. In this embodiment, placing the delivery tube in fluid communication with the tissue site may include placing the delivery tube in fluid communication with the tissue site via the manifold.

In one embodiment, a method of manufacturing a delivery tube for storing liquid from a tissue site includes forming a delivery tube having at least one lumen. The delivery tube formed in this method may be in accordance with any of the illustrative embodiments. The method may also include providing an absorbent material in a lumen. The absorbent material may be operable to absorb liquid, such as exudate, from the tissue site. The method may also include applying an absorbent material, such as absorbent material 1025 in FIG. 10, in the at least one lumen. In one embodiment, the absorbent material is an absorbent core, such as absorbent core 1325 in FIG. 13. In another embodiment, applying the absorbent material in the at least one lumen includes coating at least a portion of an inner surface of the at least one lumen with the absorbent material.

Figure 15:
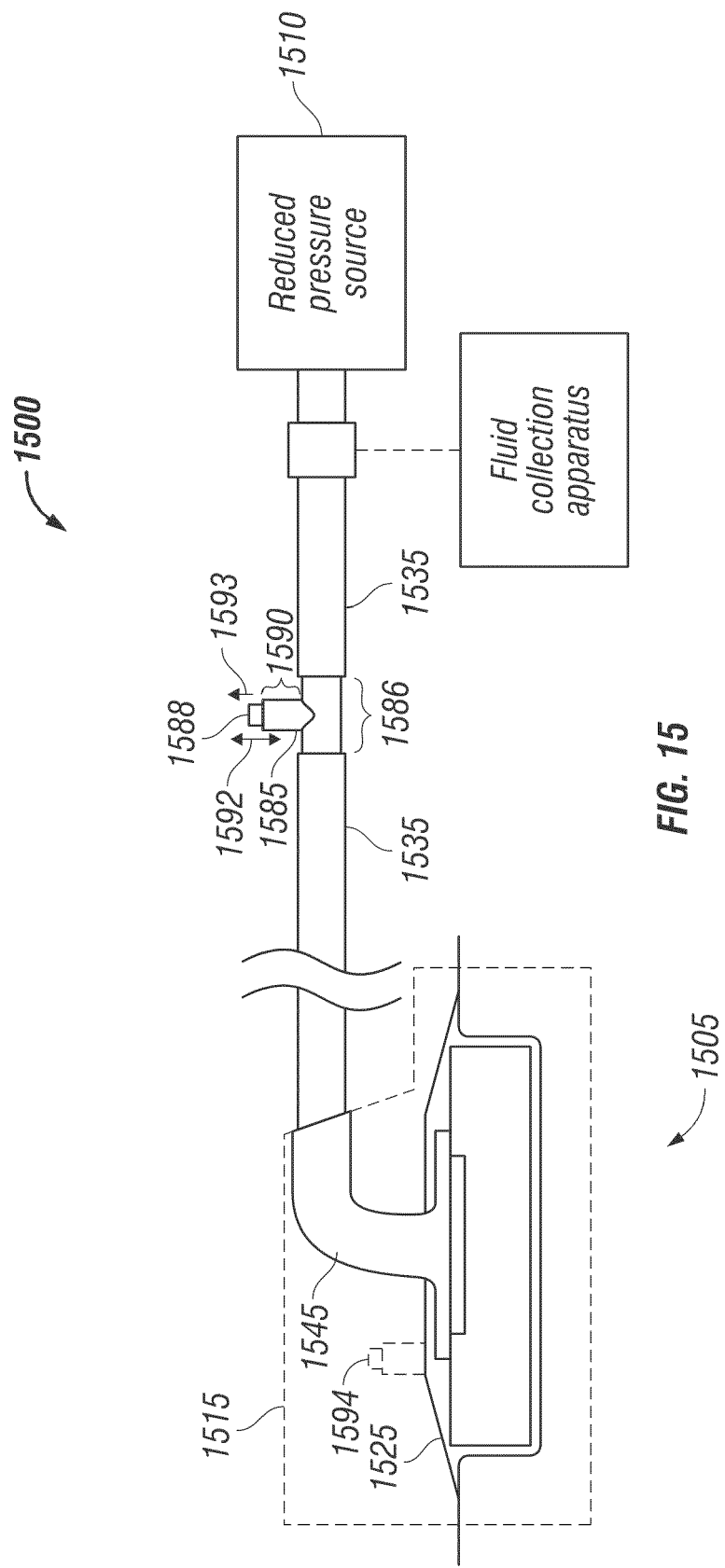
FIG. 15 is a block diagram of an apparatus for administering reduced pressure at a tissue site in accordance with an illustrative embodiment.

Turning now to FIG. 15, reduced pressure treatment system 1500, which is a non-limiting example of reduced pressure treatment system 100 in FIG. 1, is shown according to an illustrative embodiment. In particular, reduced pressure treatment system 1500 includes a non-limiting example of reduced pressure feedback system 155 in FIG. 1. Reduced pressure treatment system 1500 includes reduced pressure source 1510, which generates a reduced pressure that may be applied to tissue site 1505.

Reduced pressure treatment system 1500 also includes indicator housing 1585, which is disposed between two portions of delivery tube 1535. Delivery tube 1535 is a non-limiting example of delivery tube 135 in FIG. 1. Indicator housing 1585 includes connecting portion 1586. Connecting portion 1586 transmits the reduced pressure from one portion of delivery tube 1535 to another portion of delivery tube 1535. Connecting portion 1586 also contains a same or similar amount of reduced pressure as that contained by delivery tube 1535. Indicator housing 1585 includes indicator 1588, which is slidably coupled to an opening along tube portion 1590 of indicator housing 1585. Indicator 1588 may have a cylindrical shape. Indicator 1588 may also have an oval or polygonal cross-sectional shape. Indicator 1588 may also be any color, such as red, orange, or yellow.

Indicator 1588 responds to an amount of reduced pressure present in reduced pressure treatment system 1500 such that a user may determine whether a desired or therapeutic amount of reduced pressure is being applied to tissue site 1505. In particular, indicator 1588 is movable into a plurality of positions along axis 1592. The plurality of positions may include a retracted position. In the retracted position, indicator 1588 may be fully or partially retracted into tube portion 1590 such that indicator 1588 is partially or fully non-visible to a user. The plurality of positions may also include an extended position. In FIG. 15, indicator 1588 is shown in the extended position. In the extended position, indicator 1588 may be fully or partially protruding from tube portion 1590 such that indicator 1588 is visible by a user. The plurality of positions may also include any position between a fully extended and a fully retracted position.

Reduced pressure treatment system 1500 also includes a compressible member, such as a spring, that is coupled to indicator 1588 and is located in tube portion 1590. The compressible member is not shown in FIG. 15, but will be described in greater detail in FIGS. 16 and 17 below. The compressible member exerts a biasing force on indicator 1588 that biases indicator 1588 toward the extended position. The biasing force is exerted in the direction indicated by arrow 1593.

Although indicator housing 1585 is shown as being disposed between two portions of delivery tube 1535, indicator housing 1585 may be located anywhere in reduced pressure treatment system 1500 at which a reduced pressure being applied to tissue site 1505 may be detected. For example, indicator housing 1585, along with indicator 1588, may be located anywhere at dressing 1515, including sealing member 1525 or connector 1545. Dotted indicator 1594 shows the example in which indicator housing 1585, along with indicator 1588, is located on sealing member 1525. In another example, indicator housing 1585, along with indicator 1588, may be located on either end of a single delivery tube that couples reduced pressure source 1510 to dressing 1515.

In one embodiment, indicator 1588 moves into a retracted position in the presence of reduced pressure from reduced pressure source 1510. In particular, indicator 1588 may move into the retracted position when a reduced pressure is present in delivery tube 1535 and connecting portion 1586. In moving into the retracted position, indicator 1588 must overcome the biasing force being exerted by the compressible member in the direction indicated by arrow 1593. A sufficiently high reduced pressure in connecting portion 1586 may overcome this biasing force and pull indicator 1588 into the retracted position. The amount of reduced pressure that is required to overcome the biasing force may depend on the amount of biasing force exerted by the compressible member. In the example in which the compressible member is a coiled spring, the spring constant of the coiled spring determines the amount of reduced pressure necessary to pull indicator 1588 into the retracted position.

In one example, indicator 1588 moves into the retracted position when the reduced pressure in delivery tube 1535 exceeds a first threshold reduced pressure. The first threshold reduced pressure may be determined by a user and may be implemented by varying the biasing force exerted by the compressible member. For example, a user may select a compressible member with a spring constant that requires the reduced pressure in delivery tube 1535 to exceed a therapeutic reduced pressure in order for indicator 1588 to be pulled into the retracted position. In one embodiment, indicator 1588 moves into the retracted position when a gauge pressure generated by the reduced pressure source is equal to or less than approximately −125 millimeters of mercury. Thus, a user of reduced pressure treatment system 1500 may be able to visually detect when a therapeutic reduced pressure is being applied to tissue site 1505 by observing that indicator 1588 does not protrude from tube portion 1590.

In another embodiment, the compressible member may bias indicator 1588 into the extended position when the reduced pressure in delivery tube 1535 is less than a second threshold reduced pressure. In one example, the first threshold reduced pressure is the same as the second threshold reduced pressure. In another example, the first threshold reduced pressure is different from the second threshold reduced pressure such that the indicator is in a fully retracted position when the reduced pressure exceeds the first reduced pressure threshold and is in a fully extended position when the reduced pressure is less than the second reduced pressure threshold. In this embodiment, indicator 1588 may be in an intermediate position between the fully retracted and the fully extended position when the reduced pressure is between the first and second reduced pressure thresholds.

In another embodiment, compressible member biases indicator 1588 into the extended position in an absence of reduced pressure in delivery tube 1535. In one example, the absence of reduced pressure is due to reduced pressure source 1510 being turned off. Because the compressible member in tube portion 1590 biases indicator 1588 to protrude from tube portion 1590 when the reduced pressure is absent or below a threshold amount, a user may visually detect when a therapeutic pressure is not being applied to tissue site 1505 by observing that indicator 1588 protrudes from tube portion 1590. The user may then take the necessary action to apply a therapeutic pressure to tissue site 1505. One reason why the reduced pressure in delivery tube 1535 may be absent or below a threshold amount is because of a leak in delivery tube 1535 or elsewhere in reduced pressure treatment system 1500. In this circumstance, a user is alerted to a possible leakage when indicator 1588 is in the extended position.

Figure 16:
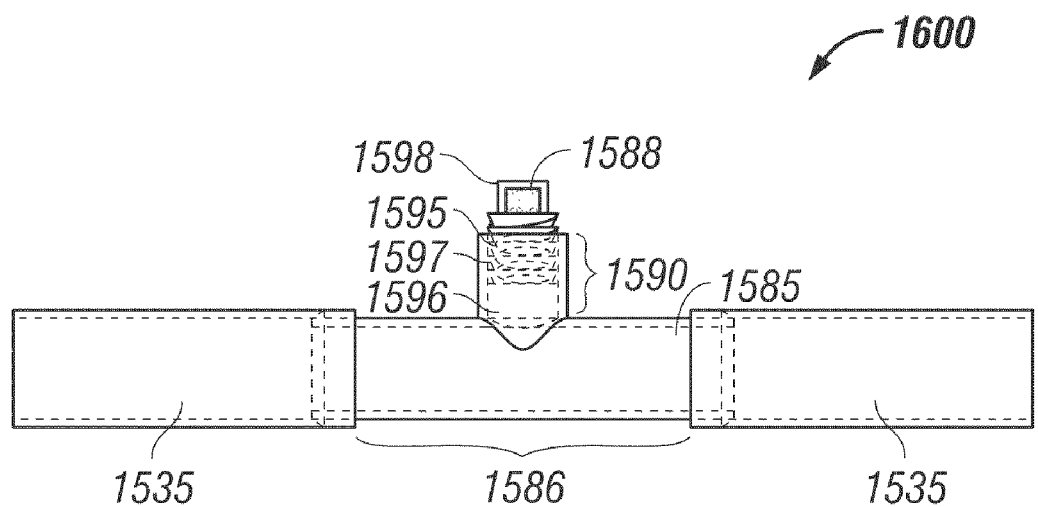
FIG. 16 is a perspective view of components of an apparatus for administering reduced pressure at a tissue site in accordance with an illustrative embodiment.

Turning now to FIG. 16, a reduced pressure feedback system 1600, such as that shown in FIG. 15, is shown in accordance with an illustrative embodiment. In particular, indicator 1588 is in an extended position in reduced pressure feedback system 1600.

Connecting portion 1586 is slidingly engaged with the two portions of delivery tube 1535 to form a sealed fit. Connecting portion 1586 of indicator housing 1585 may also be sealingly engaged with the two portions of delivery tube 1535 in a variety of ways. For example, connecting portion 1586 may be welded, screwed, glued, bolted, air-lock sealed, or snapped to the two portions of delivery tube 1535.

In reduced pressure feedback system 1600, the compressible member is a coiled spring. Tube portion 1590 of indicator housing 1585 includes base 1596, to which an end of coiled spring 1595 is coupled. However, the end of coiled spring 1595 that is not attached to indicator 1588 may be attached to any other component of indicator housing with which a coiled spring may be used to exert a biasing force on indicator 1588. The inner surface of tube portion 1590 is a tubular opening along which indicator 1588 may slide into retracted and extended positions. Coiled spring 1595 is contained by a plurality of corrugations 1597 that form part of a tubular wall. Corrugations 1597 allow the tubular wall to be compressed and expanded without causing lateral stress to the inner wall of tube portion 1590.

Reduced pressure feedback system 1600 also includes cap 1598. Cap 1598 may be composed of a transparent material that allows a user to view indicator 1588 when indicator 1588 is in the extended position. In one example, cap 1598 is also sealingly engaged with the remainder of indicator housing 1585 so that reduced pressure does not escape through the tubular opening in indicator housing 1585.

As discussed above, coiled spring 1595 may have any spring constant. The spring constant of coiled spring 1595 determines the biasing force that is exerted upon indicator 1588 toward the extended position. In one embodiment, coiled spring 1595 has a spring constant such that coiled spring 1595 biases indicator 1588 into the extended position when a gauge pressure in delivery tube 1535 exceeds approximately −125 millimeters of mercury. Other coiled springs having other spring constants may also be used to bias indicator 1588 into the extended position when the absolute pressure in delivery tube 1535 exceeds other absolute pressure thresholds, such as desired therapeutic pressure thresholds.

Figure 17:
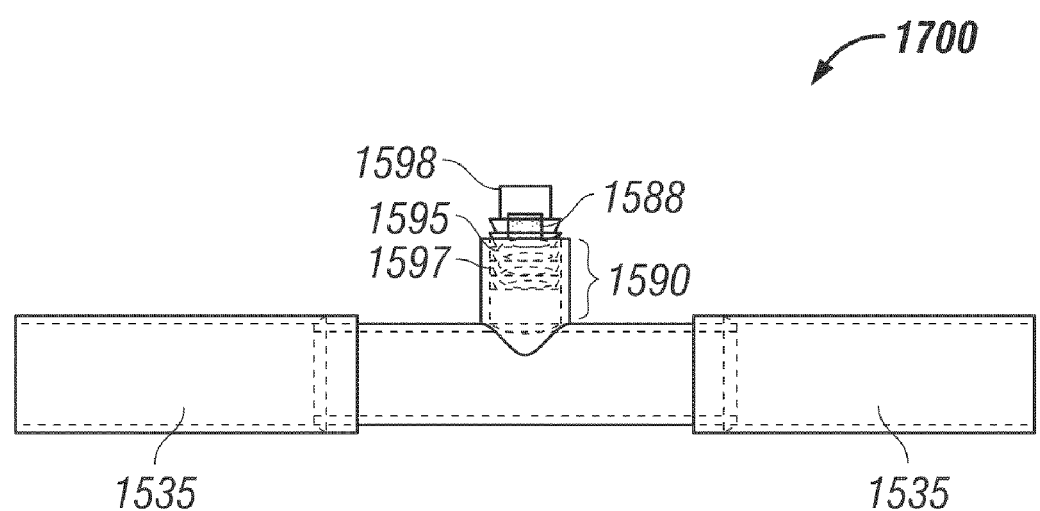
FIG. 17 is a perspective view of components of an apparatus for administering reduced pressure at a tissue site in accordance with an illustrative embodiment.

Turning now to FIG. 17, reduced pressure feedback system 1700, which is a non-limiting example of reduced pressure feedback system 1600, is shown in accordance with an illustrative embodiment. In particular, reduced pressure feedback system 1700 shows indicator 1588 in a retracted position. When indicator 1588 is in a retracted position, reduced pressure from delivery tube 1535 is transferred to indicator 1588 through the tubular wall formed from corrugations 1597. This reduced pressure exerts a pulling force upon indicator 1588 that is sufficient to overcome the biasing force exerted by coiled spring 1595 in the opposite direction. Indicator 1588 is thus pulled out of transparent cap 1598 and out of the view of a user of the reduced pressure treatment system. The absence of indicator 1588 from cap 1598 indicates to a user that a therapeutic pressure is being administered to the tissue site. In another embodiment, cap 1598 may be coupled to indicator 1588 such that cap 1598 is also retracted into tube portion 1590 when indicator 1588 is in the retracted position.

Figure 18:
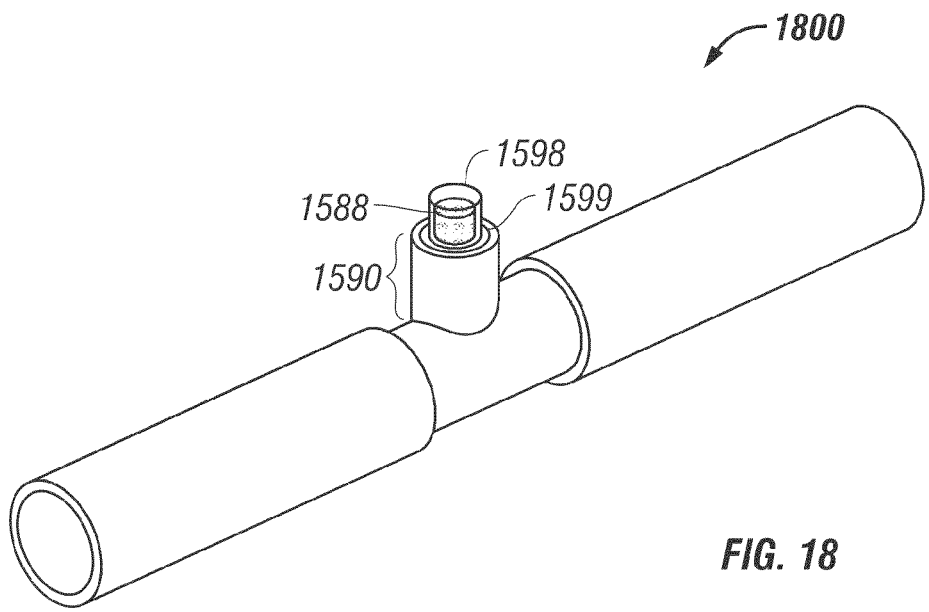
FIG. 18 is a perspective view of components of an apparatus for administering reduced pressure at a tissue site in accordance with an illustrative embodiment.

Turning now to FIG. 18, reduced pressure feedback system 1800, which is a non-limiting example of the reduced pressure feedback system shown in FIG. 15, is shown in an illustrative embodiment. The perspective view of FIG. 18 shows the circular cross-section of indicator 1588, cap 1598, tube portion 1590, as well as opening 1599 through which indicator 1588 protrudes. These components, however, may have any cross-sectional shape, such as an oval or polygon.

Figure 19:
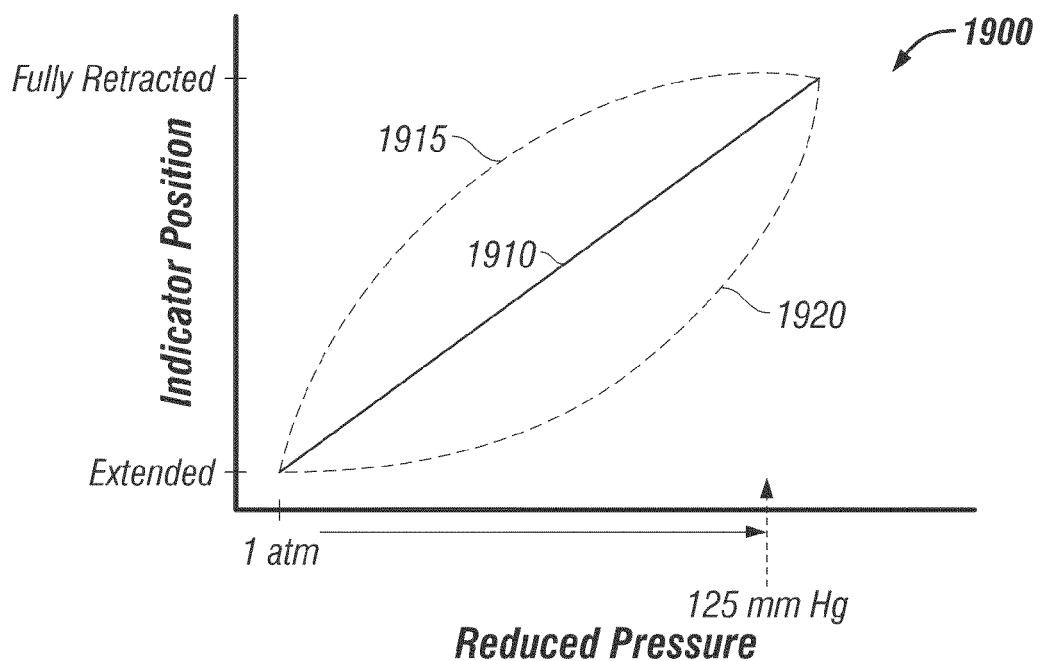
FIG. 19 is graphical representation of a system for administering reduced pressure at a tissue site in accordance with an illustrative embodiment.

Turning now to FIG. 19, a graph showing the relation between the reduced pressure in delivery tube 1535 and the position of indicator 1588 (as shown in FIG. 15) is shown in accordance with an illustrative embodiment. As shown in graph 1900, as the reduced pressure in delivery tube 1535 increases, indicator 1588 moves toward the fully retracted position. In one embodiment, indicator 1588 moves toward the full retracted position in a linear fashion as indicated by graph line 1910. The relation between the reduced pressure and the position of indicator 1588 may also follow other patterns, as indicated by graph lines 1915 and 1920. Other patterns, such as a stair-step pattern, may also characterize the relation between the reduced pressure and the position of indicator 1588. In one example, indicator 1588 is in the fully retracted position when the reduced pressure corresponds to an absolute pressure of 125 millimeters of mercury.

Figure 20:
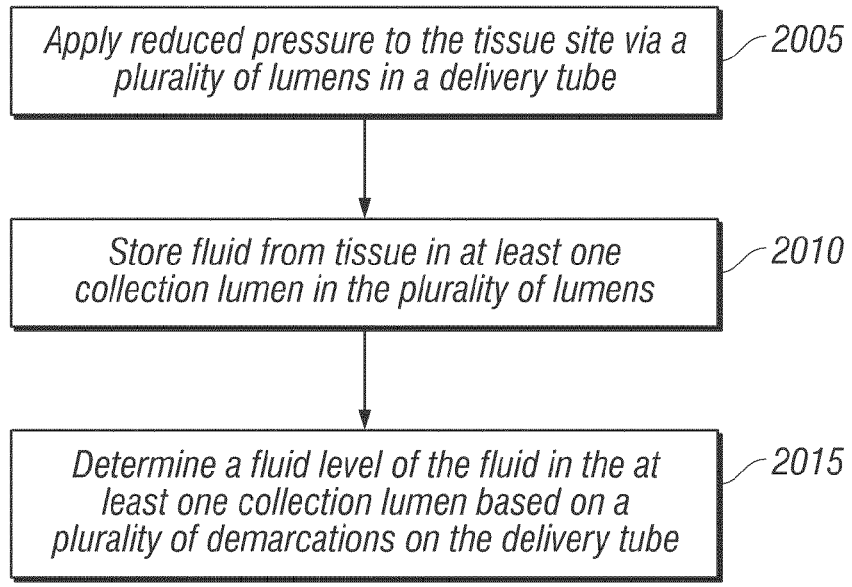
FIG. 20 is a flowchart illustrating a process for administering reduced pressure at a tissue site in accordance with an illustrative embodiment.

Turning now to FIG. 20, a process that may be implemented by a reduced pressure treatment system, such as reduced pressure treatment system 200 in FIG. 2 is shown in accordance with an illustrative embodiment. The process applies reduced pressure to a tissue site via a plurality of lumens in a delivery tube (step 2005). The process stores fluid from the tissue site in at least one collection lumen in the plurality of lumens (step 2010). The process determines a fluid level of the fluid in the at least one collection lumen based on a plurality of demarcations on the delivery tube (step 2015).

Figure 21:
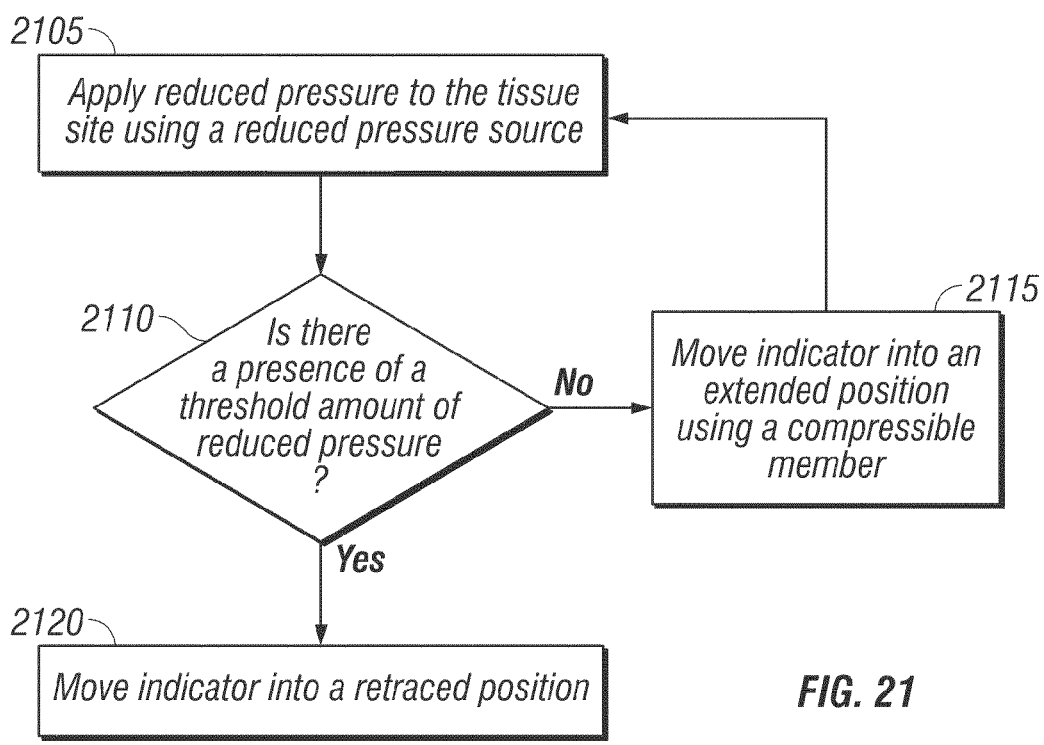
FIG. 21 is a flowchart illustrating a process for administering reduced pressure at a tissue site in accordance with an illustrative embodiment.

Turning now to FIG. 21, a process that may be implemented by a reduced pressure treatment system, such as reduced pressure treatment system 1000 in FIG. 10 is shown in accordance with an illustrative embodiment. The process applies a reduced pressure to the tissue site using a reduced pressure source (step 2105). The process determines whether there is a presence of a threshold amount of reduced pressure in a delivery tube or other component of a reduced pressure treatment system (step 2110). If the process determines that there is not a presence of a threshold amount of reduced pressure, the process moves an indicator into an extended position using a compressible member. The process then returns to step 2105. Returning to step 2110, if the process determines that there is a presence of a threshold amount of reduced pressure, the process moves the indicator into the retracted position (step 2120).

The flowcharts and block diagrams in the different depicted embodiments illustrate the architecture, functionality, and operation of some possible implementations of the apparatus and methods. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

I claim:

1. A system for storing liquid from a tissue site, the system comprising:
    a reduced pressure source operable to supply reduced pressure;
    a manifold adapted to distribute the reduced pressure;
    a delivery tube having at least one lumen, the delivery tube operable to transmit the reduced pressure from the reduced pressure source to the manifold, the delivery tube operable to receive the liquid from the tissue site via the manifold;
    wherein the at least one lumen has a plurality of ribs and recesses; and
    an absorbent material disposed in the at least one lumen in at least the plurality of recesses, the absorbent material operable to absorb the liquid from the tissue site.

2. An apparatus for storing liquid from a tissue site, the apparatus comprising:
    a delivery tube having at least one lumen, the delivery tube operable to transmit reduced pressure to the tissue site and to receive liquid from the tissue site;
    wherein the at least one lumen has a plurality of recesses; and
    an absorbent material disposed in the at least one lumen in at least the plurality of recesses, the absorbent material operable to absorb the liquid from the tissue site.

3. The apparatus of claim 2, wherein the absorbent material at least partially covers an inner surface of the at least one lumen.

4. The apparatus of claim 2, wherein the at least one lumen includes a plurality of ribs, and wherein the plurality of recesses are separated from one another by a rib in the plurality of ribs.

5. The apparatus of claim 4, wherein the absorbent material is disposed in all of the plurality of recesses.

6. The apparatus of claim 4, wherein the at least one lumen includes a central reduced pressure passage when the absorbent material is saturated with the liquid from the tissue site.

7. The apparatus of claim 2, wherein at least one wall of each of the plurality of recesses has a substantially semi-circular cross-sectional shape.

8. The apparatus of claim 7, wherein each of the plurality of recesses is an elongated recess that extends along at least a portion of the length of the delivery tube.

9. The apparatus of claim 8, wherein each of the plurality of recesses extends along an entire length of the delivery tube.

10. The apparatus of claim 3, wherein the absorbent material covers an entire inner surface of the at least one lumen.

11. The apparatus of claim 2, wherein the absorbent material is an absorbent core disposed in the at least one lumen.

12. The apparatus of claim 11, wherein the absorbent core expands as the absorbent core absorbs liquid from the tissue site.

13. The apparatus of claim 11, wherein the absorbent core is a cylindrical absorbent core, and wherein the cylindrical absorbent core is flexible.

14. The apparatus of claim 13, wherein the absorbent core has a substantially circular cross-sectional shape.

15. The apparatus of claim 11, wherein at least one of the plurality of recesses is a reduced pressure delivery recess for delivering the reduced pressure, and wherein the liquid from the tissue site is unable to enter the reduced pressure delivery recess.

16. The apparatus of claim 15, wherein at least one of the plurality of recesses is a collection recess for storing liquid from the tissue site.

17. The apparatus of claim 2, wherein the liquid is exudate from a wound.

18. The apparatus of claim 2, wherein the absorbent material includes at least one of super absorbent fiber, super absorbent particulates, hydrofiber, sodium carboxymethyl cellulose, and alginates.

19. A system for storing liquid from a tissue site, the system comprising:
    a reduced pressure source operable to supply reduced pressure;
    a manifold adapted to distribute the reduced pressure;
    a delivery tube having at least one lumen, the delivery tube operable to transmit the reduced pressure from the reduced pressure source to the manifold, the delivery tube operable to receive the liquid from the tissue site via the manifold; and
    wherein the at least one lumen is formed with a plurality of recesses; and
    an absorbent material covering the plurality of recesses.

* * * * *

UNITED STATES PATENT AND TRADEMARK OFFICE
Certificate

Patent No. 8,267,908 B2　　　　　　　　　　　　　　　　Patented: September 18, 2012

On petition requesting issuance of a certificate for correction of inventorship pursuant to 35 U.S.C. 256, it has been found that the above identified patent, through error and without any deceptive intent, improperly sets forth the inventorship.
 Accordingly, it is hereby certified that the correct inventorship of this patent is: Richard Daniel John Coulthard, Verwood (GB); Timothy Mark Robinson, Basingstoke (GB); Christopher Brian Locke, Bournemouth (GB); and Aidan Marcus Tout, Alderbury (GB).

Signed and Sealed this Twelfth Day of March 2013.

<div style="text-align:right">

TATYANA ZALUKAEVA
*Supervisory Patent Examiner*
Art Unit 3761
Technology Center 3700

</div>